US005830675A

United States Patent [19]
Targan et al.

[11] Patent Number: 5,830,675
[45] Date of Patent: Nov. 3, 1998

[54] METHODS FOR SELECTIVELY DETECTING PERINUCLEAR ANTI-NEUTROPHIL CYTOPLASMIC ANTIBODY OF ULCERATIVE COLITIS, PRIMARY SCLEROSING CHOLANGITIS, OR TYPE 1 AUTOIMMUNE HEPATITIS

[75] Inventors: Stephan R. Targan, Los Angeles; Alda Vidrich, Pacific Palisades, both of Calif.

[73] Assignee: Cedars-Sinai Medical Center, Los Angeles, Calif.

[21] Appl. No.: 480,753

[22] Filed: Jun. 7, 1995

Related U.S. Application Data

[63] Continuation-in-part of Ser. No. 320,163, Oct. 7, 1994, which is a continuation of Ser. No. 28,784, Mar. 10, 1993, abandoned.

[51] Int. Cl.⁶ .......................... G01N 33/53; G01N 33/555; G01N 33/567
[52] U.S. Cl. .......................... 435/7.24; 435/7.9; 435/188; 435/7.21; 436/548
[58] Field of Search ..................................... 435/7.24, 7.9, 435/188, 810, 961, 962, 967; 436/175, 519, 811, 825, 176

[56] References Cited

U.S. PATENT DOCUMENTS

| 5,238,813 | 8/1993 | Lefkowith | 435/7.21 |
| 5,292,667 | 3/1994 | Podolsky et al. | 436/548 |

FOREIGN PATENT DOCUMENTS

| 615129 | 9/1994 | European Pat. Off. . |
| WO 9106572 | 5/1991 | WIPO . |
| WO 9202819 | 2/1992 | WIPO . |
| WO 9312248 | 6/1993 | WIPO . |

OTHER PUBLICATIONS

Mulder, A.H.L., et al., "Antineutrophil Antibodies in Inflammatory Bowel Disease Recognize Different Antigens." *Adv. Exp. Med. Biol.,* 336: 519–522 (1993).

Mulder, A.H.L., et al., "Prevalence and Characterization of Neutrophil Cytoplasmic Antibodies in Autoimmune Liver Diseases." *Hepatology,* 17(3): 411–417 (1993).

O'Mahony, S., et al., "Systemic and Mucosal Antibodies to Klebsiella in Patients with Ankylosing Spondylitis and Crohn's Disease." *Ann. Rheum. Dis.,* 51: 1296–1300 (1992).

O'Shea, J.J., et al., "Evidence for Distinct Intracellular Pools of Receptors for C3b and C3bi in Human Neutrophils." *J. Immunol.,* 134(4): 2580–2587 (1985).

Poralla, T., et al., "The Asialoglycoprotein Receptor as Target Structure in Autoimmune Liver Disease." *Seminars in Liver Diseases,* 11(3): 215–222 (1991).

Rabinovitz, M., et al., "Simultaneous Occurrence of Primary Sclerosing Cholangitis and Autoimmune Chronic Active Hepatitis in a Patient with Ulcerative Colitis." *Dig. Dis. Sci.,* 37(10): 1606–1611 (1992).

Saxon, A., et al., "A Distinct Subset of Antineutrophil Cytoplasmic Antibodies Is Associated with Inflammatory Bowel Disease." *J. Allergy Clin. Immunol.,* 86(2): 202–210 (1990).

Schalm, S.W., et al., "Severe Chronic Active Liver Disease; Prognostic Significance of Initial Morphologic Patterns." *Digestive Diseases,* 22(11): 973–980 (1977).

Senécal, J., et al., "Autoantibodies to Major and Minor Nuclear Lamins Are Not Restricted to Autoimmune Diseases." *Clin. Immunol. Immunopath.,* 63(2): 115–125 (1992).

Bennett, R.M. et al. Brit. J. Haematol., vol. 63, pp. 105–117, 1986.

Briggs, R.C. et al. J. Histochem. Cytochem., vol. 29, No. 10, pp. 1128–1136, 1981.

Chaly, N. et al. Can. J. Biochem. Cell Biol., vol. 63, pp. 644–653, 1985.

Cohen Tervaert, J.W. et al. Gastroenterology, vol. 102, No. 3, p. 1090, 1992.

Das, K.M., et al., "The Production and Characterization of Monoclonal Antibodies to A Human Colonic Antigen Associated with Ulcerative Colitis: Cellular Localization of the Antigen by Using the Monoclonal Antibody," *J. Immunology,* 139(1): 77–84 (1987).

Das, K.M., et al., "A Shared and Unique Epitope(s) on Human Colon, Skin, and Biliary Epithelium Detected by a Monoclonal Antibody." *Gastroenterology,* 98: 464–469 (1990).

Duerr, R.H., et al., "Neutrophil Cytoplasmic Antibodies: A Link Between Primary Sclerosing Cholangitis and Ulcerative Colitis." *Gastroenterology,* 100: 1385–1391 (1991).

Duerr, R.H., et al., "Anti–Neutrophil Cytoplasmic Antibodies in Ulcerative Colitis. Comparison With Other Colitides/Diarrheal Illnesses." *Gastroenterology,* 100: 1590–1596 (1991).

Eggena, M., et al., "Characterization of Ulcerative Colitis Specific pANCA Using Phage Display Technology." *F. Amer. Society of Exper. Biol., J* 8(5): A1010 (1994).

Elsaghier, A., et al., "Antibodies to *Mycobacterium Paratuberculosis*–Specific Protein Antigens in Crohn's Disease." *Clin. Exp. Immunol.,* 90: 503–508 (1992).

Farrant, J.M., et al., "HLA DR2 is a Susceptibility Marker for UC in British Patients Irrespective of ANCA Positivity." *Immunol. Microbio. Inflamm. Disorders,* A679 (1994).

(List continued on next page.)

*Primary Examiner*—James C. Housel
*Assistant Examiner*—Ginny Allen Portner
*Attorney, Agent, or Firm*—Campbell & Flores LLP

[57] ABSTRACT

The invention is directed to methods and kits for detecting and measuring the presence or absence of perinuclear anti-neutrophil cytoplasmic antibody of ulcerative colitis, primary sclerosing cholangitis or type 1 autoimmune hepatitis. The methods and kits of the present invention provide safe and reliable means for diagnosing ulcerative colitis, primary sclerosing cholangitis, and type 1 autoimmune hepatitis. The antigens reactive with perinuclear anti-neutrophil cytoplasmic autoantibody of ulcerative colitis and primary sclerosing cholangitis are also provided.

24 Claims, 3 Drawing Sheets

OTHER PUBLICATIONS

Gross, V.L., et al., "ANCA and associated diseases: immunodiagnostic and pathogenetic aspects." *Clin. Exp Immunol.*, 91: 1–12 (1993).

Halbwachs–Mecarelli, L., et al., "Antineutrophil Cytoplasmic Antibodies (ANCA) Directed Against Cathepsin G in Ulcerative Colitis, Crohn's Disease and Primary Sclerosing Cholangitis." *Clin. exp. Immunol.*, 90: 79–84 (1992).

Hardarson, S., et al., "Antineutrophil Cytoplasmic Antibody in Inflammatory Bowel and Hepatobiliary Diseases." *Am. J. Clin. Pathol.*, 99(3): 277–291 (1993).

Homberg, J., et al., "Chronic Active Hepatitis Associated with Antiliver/Kidney Microsome Antibody Type 1: A Second Type of 'Autoimmune' Hepatitis." *Hepatology,* 7(6): 1333–1339 (1987).

Johnson, P.J., et al., "Meeting Report: International Autoimmune Hepatitis Group." *Hepatology,* 18(4): 998–1005 (1993).

Kallenberg, C.G.M., et al., "Antineutrophil Cytoplasmic Antibodies; A Still–Growing Class of Autoantibodies in Inflammatory Disorders." *Am. J. Med.,* 93: 675–682 (1992).

King, C.H., et al., "Modulation of Human Neutrophil Effector Functions by Monoclonal Antibodies Against Surface Membrane Molecules of 94,000 and 180,000 Molecular Weight." *Blood,* 67(1): 188–194 (1986).

Lidman, K., et al., "Anti–Actin Specificity of Human Smooth Muscle Antibodies in Chronic Active Hepatitis." *Clin. Exp. Immunol.,* 24: 266–272 (1976).

Lindberg, E., et al., "Antibody (IgG, IgA, and IgM) to Baker's Yeast (*Saccharomyces cerevisiae*), Yeast Mannan, Gliadin, Ovalbumin and Betalactoglobulin in Monozygotic Twins With Inflammatory Bowel Disease." *Gut,* 33: 909–913 (1992).

Lo, S.K., et al., "Antineutrophil Antibody: a Test for Autoimmune Primary Sclerosing Cholangitis in Childhood?" *Gut,* 34: 199–202 (1993).

Maddrey, W.C., "Subdivisions of Idiopathic Autoimmune Chronic Active Hepatitis." *Hepatology,* 7(6): 1372–1375 (1987).

Billing et al., "Nuclear Localization of the Antigen Detected by Ulcerative Colitis–Asociated Perinuclear Antineutrophil Cytoplasmic Antibodies," *Am. J. of Pathology* 147:979–987 (1995).

Eggena et al., "Histone H1: The Ulcerative Colitis Specific pANCA Target Antigen," *FASEB J.* 10:A1079 (1996).

Eggena et al., "Phage Display Cloning and Characterization of an Immunogenic Marker (Perinuclear Anti–neutrophil Cytoplasmic Antibody) in Ulcerative Colitis," *J. Immunol.* 156:4005–4011 (1996).

Gur et al., "Autoantibody Profile of Primary Sclerosing Cholangitis," *Pathobiology* 63:76–82 (1995).

Monestier et al., "Deoxyribonuclease I Treatment of Histones for the Detection of Anti–histone Antibodies in Solid–phase Immunoassays," *J.Immunological Methods* 127:289–291 (1990).

Rump et al., "A New Type of Perinuclear Anti–neutrophil Cytoplasmic Antibody (p–ANCA) in Active Ulcerative Colitis but not in Crohn's Disease," *Immunobiology* 181:406–413 (1990).

Targan et al., "High–titer Antineutrophil Cytoplasmic Antibodies in Type–1 Autoimmune Hepatits," *Gastroenterology* 108:1159–1166 (1995).

Vidrich et al., "Segregation of pANCA Antigenic Recognition by DNase Treatment of Neutrophils: Ulcerative Colitis, Type I Autoimmune Hepatitis, and Primary Sclerosing Cholangitis," *J. Clinical Immunol.* 15:293–299 (1995).

Soloway, R.D., et al., "Clinical, Biochemical, and Histological Remission of Severe Chronic Active Liver Disease: A Controlled Study of Treatments and Early Prognosis." *Gastroenterology,* 63(5): 820–833 (1972).

Stechemesser, E., et al., "Characterization and Clinical Relevance of Liver–Pancreas Antibodies in Autoimmune Hepatits." *Hepatology,* 18(1): 1–9 (1993).

Stevens, T.R., et al., "Anti–Endothelial Cell Antibodies in Inflammatory Bowel Disease." *Digestive Dis. and Sci.,* 38(3): 426–432 (1993).

Summerskill, W.H.J., "Chronic Hepatitis—1975." *Digestive Diseases,* 20(11): 1087–1090 (1975).

Tahir, S.K., et al., "Nuclear Localization of UC Specific Perinuclear Antineutrophil *Cytoplasmic* Antibody (pANCA) Reactive Antigen." *Immunol. Microbio. Inflamm. Disorders,* A779 (1994).

Treichel, U., et al., "Autoantibodies to Human Asialoglycoprotein Receptor in Autoimmune–type Chronic Hepatitis." *Hepatology,* 11(4): 606–612 (1990).

Vidrich, A., et al., "IgG Subclass Distinguishes Between PSC and UC ANCA." *AASLD,* A1015 (1992).

Wiesner, R.H., et al., "Clinicopathologic Features of the Syndrome of Primary Sclerosing Cholangitis." *Gastroenterology,* 79: 200–206 (1980).

Yang, H., et al., "Ulcerative Colitis: A Genetically Heterogeneous Disorder Defined by Genetic (HLA Class II) and Subclinical (Antineutrophil Cytoplasmic Antibodies) Markers." *J. Clin. Invest.,* 92: 1080–1084 (1993).

Cambridge, G., et al., "Anti–neutrophil Antibodies in Inflammatory Bowel Disease: Prevalence and Diagnostic Role." *Gut,* 33:668–674 (1992).

Czaja, A.J., et al., "Autoimmune Features as Determinants of Prognosis in Steroid–Treated Chronic Active Hepatitis of Uncertain Etiology." *Gastroenterology,* 85: 713–717 (1983).

Czaja, A.J., "Natural History, Clinical Features, and Treatment of Autoimmune Hepatitis." *Seminars in Liver Disease,* 4(1): 1–12 (1984).

Czaja, A.J., et al., "Frequency and Significance of Antibodies to Liver/Kidney Microsome Type 1 in Adults With Chronic Active Hepatitis." *Gastroenterology,* 103: 1290–1295 (1992).

Czaja, A.J., et al., "Antibodies to Soluble Liver Antigen, P45011D6, and Mitochondrial Complexes in Chronic Hepatitis." *Gastroenterology,* 105: 1522–1528 (1993).

Czaja, A.J., et al., "Sensitivity, Specificity, and Predictability of Biopsy Interpretations in Chronic Hepatitis." *Gastroenterologty,* 105: 1824–1832 (1993).

Czaja, A.J., et al., "Genetic Predispositions for the Immunological Features of Chronic Active Hepatitis." *Hepatology,* 18(4): 816–822 (1993).

Czaja, A.J., "Chronic Active Hepatitis: The Challenge for a New Nomenclature." *Ann Intern. Med.,* 119: 510–517 (1993).

Czaja, A.J., et al., "Patterns of Nuclear Immunofluorescence and Reactivities to Recombinant Nuclear Antigens in Autoimmune Hepatitis." *Gastroenterology,* 107: 200–207 (1994).

Konstantinov, K. et al. Clin. Immunol. Immunopathol., vol. 62, No. 1, pp. 112–118, 1992.

Lassoued, K. et al. Ann. Int. Med., vol. 108, pp. 829–833, 1988.

Mayet, W.J. et al. Eur. J. Clin. Invest., vol. 20, pp. 516–524, 1990.

Mulder, A.H.L. et al. Adv. Exp. Med. Biol., vol. 336, pp. 545–549, 1993.

Peen, E. et al. Gut, vol. 34, pp. 56–62, 1993.

Senecal, J.-L,. et al. Rheumatol., vol. 20, No. 2, pp. 211–219, 1993.

Wesierska–Gadek, J. et al. Clin. Immunol. Immunolpathol., vol. 49, pp. 107–115, 1988.

Worman, H.J. and J.-C. Courvalin. Hepatology, vol. 14, No. 6, pp. 1269–1279, 1991.

Zauli, D. et al. Gastroenterology, vol. 102, pp. 1088–1095, 1992.

Oudkerk–Pool, M. et al, Gut, Jan. 1993, vol. 34, p. 46–50.

Rump, JA et al, Immunobiol, vol. 181, pp. 406–413, 1990.

Contreras, TJ et al, Transfusion, vol. 20(5) 1980, pp. 519–530.

Rao, KMK, J. Gerontol, vol. 41(5) 1986, pp. 561–566.

Matulskaia, LI et al, Vopr Med. Khim, Jan.–Feb. 1986, vol. 32(1), pp. 32–34, (Abstract English).

Jack, RM et al, J. Immunol, vol. 137(12), 1986, p. 3996–p. 4003.

Strauss, RG et al, J. Reticuloendothelial Soc., vol. 23(3), Mar. 1978.

Lamers, MC. et al, Eur. J. Immunology, 1981, vol. 11, p. 757–764.

Rump et al, Immunologly, vol. 184, pp. 406–413, 1990.

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 699 base pairs
        ( B ) TYPE: nucleic acid
        ( C ) STRANDEDNESS: double
        ( D ) TOPOLOGY: circular ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens
        ( F ) TISSUE TYPE: Gut-associated lymphoid
        ( G ) CELL TYPE: Lymphocyte ( v i i i ) IMMEDIATE SOURCE:
        ( B ) CLONE: 5-3

( i x ) FEATURE:
        ( A ) NAME/KEY: CDS
        ( B ) LOCATION: 1..699
        ( D ) OTHER INFORMATION: /codon_start= 1
            / product= "Human Heavy Chain of IgG ANCA
            associated with UC"

( i x ) FEATURE:
        ( A ) NAME/KEY: misc_RNA
        ( B ) LOCATION: 1..15
        ( D ) OTHER INFORMATION: /product="N-Terminal Tag"

( i x ) FEATURE:
        ( A ) NAME/KEY: misc_RNA
        ( B ) LOCATION: 16..96
        ( D ) OTHER INFORMATION: /label=FR1
            / note= ""FR1"refers to Framework Region 1"

( i x ) FEATURE:
        ( A ) NAME/KEY: misc_RNA
        ( B ) LOCATION: 97..111
        ( D ) OTHER INFORMATION: /label=CDR1
            / note= ""CDR1"refers to Complimentarity
            Determining Region 1"

( i x ) FEATURE:

(A) NAME/KEY: misc_RNA
                (B) LOCATION: 112..153
                (D) OTHER INFORMATION: /label=FR2
                        / note= ""FR2"refers to Framework Region 2"

( i x ) FEATURE:
                (A) NAME/KEY: misc_RNA
                (B) LOCATION: 154..204
                (D) OTHER INFORMATION: /label=CDR2
                        / note= ""CDR2"refers to Complimentarity
                        Determining Region 2"

( i x ) FEATURE:
                (A) NAME/KEY: misc_RNA
                (B) LOCATION: 205..300
                (D) OTHER INFORMATION: /label=FR3
                        / note= ""FR3"refers to Framework Region 3"

( i x ) FEATURE:
                (A) NAME/KEY: misc_RNA
                (B) LOCATION: 301..327
                (D) OTHER INFORMATION: /label=CDR3
                        / note= ""CDR3"refers to Complimentarity
                        Determining Region 3"

( i x ) FEATURE:
                (A) NAME/KEY: misc_RNA
                (B) LOCATION: 328..360
                (D) OTHER INFORMATION: /label=FR4
                        / note= ""FR4"refers to Framework Region 4"

( i x ) FEATURE:
                (A) NAME/KEY: misc_RNA
                (B) LOCATION: 361..651
                (D) OTHER INFORMATION: /label=CH1
                        / note= ""CH1"refers to Constant Segment 1 of the
                        Heavy Chain"

( i x ) FEATURE:
                (A) NAME/KEY: misc_RNA
                (B) LOCATION: 652..678
                (D) OTHER INFORMATION: /label=Hinge
                        / note= ""Hinge"refers to Partial Hinge Segment of
                        the Heavy Chain"

( i x ) FEATURE:
                (A) NAME/KEY: misc_RNA
                (B) LOCATION: 679..699
                (D) OTHER INFORMATION: /label=Hex-HTAG
                        / note= ""Hex-HTAG"refers to Hexahistidine Tag"

( i x ) FEATURE:
                (A) NAME/KEY: misc_RNA
                (B) LOCATION: 16..651
                (D) OTHER INFORMATION: /label=Fd
                        / note= ""Fd"refers to the Fd of the Heavy Chain"

( i x ) FEATURE:
                (A) NAME/KEY: misc_RNA
                (B) LOCATION: 16..300
                (D) OTHER INFORMATION: /label=VHSEGMENT
                        / note= ""VHSEGMENT"refers to Variable Segment of
                        the Heavy Chain"

( i x ) FEATURE:
                (A) NAME/KEY: misc_RNA
                (B) LOCATION: 301..315
                (D) OTHER INFORMATION: /label=D
                        / note= ""D"refers to Diversity Segment"

( i x ) FEATURE:
                (A) NAME/KEY: misc_RNA
                (B) LOCATION: 316..360
                (D) OTHER INFORMATION: /label=JH
                        / note= ""JH"refers to Joining Segment of the
                        Heavy Chain"

( i x ) FEATURE:
                (A) NAME/KEY: misc_RNA
                (B) LOCATION: 16..360

( D ) OTHER INFORMATION: /label=VHDOMAIN
/ note= ""VHDOMAIN"refers to Variable Domain of the Heavy Chain"

( x i ) SEQUENCE DESCRIPTION: SEQ ID NO:1:

| GCC | CAG | GTG | AAA | CTG | CTC | GAG | CAG | TCT | GGG | GGA | GGC | GTG | GTC | CAG | CCT | 48 |
| Ala | Gln | Val | Lys | Leu | Leu | Glu | Gln | Ser | Gly | Gly | Gly | Val | Val | Gln | Pro | |
| 1 | | | | 5 | | | | | 10 | | | | | 15 | | |

| GGG | AAG | TCC | CTG | AGA | CTC | TCC | TGT | GCA | GCC | TCT | GGA | TTC | ACC | TTC | AGG | 96 |
| Gly | Lys | Ser | Leu | Arg | Leu | Ser | Cys | Ala | Ala | Ser | Gly | Phe | Thr | Phe | Arg | |
| | | | 20 | | | | | 25 | | | | | 30 | | | |

| AAC | TAT | GGC | ATG | CAC | TGG | GTC | CGG | CAG | GCT | CCA | GGC | AAG | GGG | CTG | GAG | 144 |
| Asn | Tyr | Gly | Met | His | Trp | Val | Arg | Gln | Ala | Pro | Gly | Lys | Gly | Leu | Glu | |
| | | 35 | | | | | 40 | | | | | 45 | | | | |

| TGG | GTG | GCA | GGT | ATT | TCC | TCT | GAT | GGA | AGA | AAA | AAA | AAG | TAT | GTA | GAC | 192 |
| Trp | Val | Ala | Gly | Ile | Ser | Ser | Asp | Gly | Arg | Lys | Lys | Lys | Tyr | Val | Asp | |
| | 50 | | | | | 55 | | | | | 60 | | | | | |

| TCC | GTG | AAG | GGC | CGA | TTC | ACC | ATC | TCC | AGA | GAC | AAG | TCC | AAG | AAC | ACG | 240 |
| Ser | Val | Lys | Gly | Arg | Phe | Thr | Ile | Ser | Arg | Asp | Lys | Ser | Lys | Asn | Thr | |
| 65 | | | | | 70 | | | | | 75 | | | | | 80 | |

| CTG | TAT | CTG | CAA | ATG | AAC | AGC | CTC | AGA | GCT | GAG | GAC | ACG | GCT | GTG | TAT | 288 |
| Leu | Tyr | Leu | Gln | Met | Asn | Ser | Leu | Arg | Ala | Glu | Asp | Thr | Ala | Val | Tyr | |
| | | | | 85 | | | | | 90 | | | | | 95 | | |

| TAC | TGT | GCG | AAA | TTG | TCC | CGC | GCG | GGT | GGT | TTT | GAC | ATC | TGG | GGC | CAA | 336 |
| Tyr | Cys | Ala | Lys | Leu | Ser | Arg | Ala | Gly | Gly | Phe | Asp | Ile | Trp | Gly | Gln | |
| | | | 100 | | | | | 105 | | | | | 110 | | | |

| GGG | ACA | ATG | GTC | ACC | GTC | TCT | TCA | GCC | TCC | ACC | AAG | GGC | CCA | TCG | GTC | 384 |
| Gly | Thr | Met | Val | Thr | Val | Ser | Ser | Ala | Ser | Thr | Lys | Gly | Pro | Ser | Val | |
| | | 115 | | | | | 120 | | | | | 125 | | | | |

| TTC | CCC | CTG | GCA | CCC | TCC | TCC | AAG | AGC | ACC | TCT | GGG | GGC | ACA | GCG | GCC | 432 |
| Phe | Pro | Leu | Ala | Pro | Ser | Ser | Lys | Ser | Thr | Ser | Gly | Gly | Thr | Ala | Ala | |
| | 130 | | | | | 135 | | | | | 140 | | | | | |

| CTG | GGC | TGC | CTG | GTC | AAG | GAC | TAC | TTC | CCC | GAA | CCG | GTG | ACG | GTG | TCG | 480 |
| Leu | Gly | Cys | Leu | Val | Lys | Asp | Tyr | Phe | Pro | Glu | Pro | Val | Thr | Val | Ser | |
| 145 | | | | | 150 | | | | | 155 | | | | | 160 | |

| TGG | AAC | TCA | GGC | GCC | CTG | ACC | AGC | GGC | GTG | CAC | ACC | TTC | CCG | GCT | GTC | 528 |
| Trp | Asn | Ser | Gly | Ala | Leu | Thr | Ser | Gly | Val | His | Thr | Phe | Pro | Ala | Val | |
| | | | | 165 | | | | | 170 | | | | | 175 | | |

| CTA | CAG | TCC | TCA | GGA | CTC | TAC | TCC | CTC | AGC | AGC | GTG | GTG | ACC | GTG | CCC | 576 |
| Leu | Gln | Ser | Ser | Gly | Leu | Tyr | Ser | Leu | Ser | Ser | Val | Val | Thr | Val | Pro | |
| | | | 180 | | | | | 185 | | | | | 190 | | | |

| TCC | AGC | AGC | TTG | GGC | ACC | CAG | ACC | TAC | ATC | TGC | AAC | GTG | AAT | CAC | AAG | 624 |
| Ser | Ser | Ser | Leu | Gly | Thr | Gln | Thr | Tyr | Ile | Cys | Asn | Val | Asn | His | Lys | |
| | | 195 | | | | | 200 | | | | | 205 | | | | |

| CCC | AGC | AAC | ACC | AAG | GTG | GAC | AAG | AAA | GCA | GAG | CCC | AAA | TCT | TGT | GAC | 672 |
| Pro | Ser | Asn | Thr | Lys | Val | Asp | Lys | Lys | Ala | Glu | Pro | Lys | Ser | Cys | Asp | |
| | 210 | | | | | 215 | | | | | 220 | | | | | |

| AAA | ACT | AGT | CAC | CAC | CAC | CAC | CAC | CAC | | | | | | | | 699 |
| Lys | Thr | Ser | His | His | His | His | His | His | | | | | | | | |
| 225 | | | | | 230 | | | | | | | | | | | |

( 2 ) INFORMATION FOR SEQ ID NO:2:

( i ) SEQUENCE CHARACTERISTICS:
        ( A ) LENGTH: 233 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Ala | Gln | Val | Lys | Leu | Leu | Glu | Gln | Ser | Gly | Gly | Gly | Val | Val | Gln | Pro |
| 1 | | | | 5 | | | | | 10 | | | | | 15 | |

| | | | | | | | | | | | | | | |
|---|---|---|---|---|---|---|---|---|---|---|---|---|---|---|
|Gly|Lys|Ser|Leu|Arg|Leu|Ser|Cys|Ala|Ala|Ser|Gly|Phe|Thr|Phe|Arg|
| | | |20| | | |25| | | | |30| | |
|Asn|Tyr|Gly|Met|His|Trp|Val|Arg|Gln|Ala|Pro|Gly|Lys|Gly|Leu|Glu|
| | |35| | | |40| | | | |45| | | |
|Trp|Val|Ala|Gly|Ile|Ser|Ser|Asp|Gly|Arg|Lys|Lys|Lys|Tyr|Val|Asp|
| |50| | | |55| | | | |60| | | | |
|Ser|Val|Lys|Gly|Arg|Phe|Thr|Ile|Ser|Arg|Asp|Lys|Ser|Lys|Asn|Thr|
|65| | | | |70| | | |75| | | | |80|
|Leu|Tyr|Leu|Gln|Met|Asn|Ser|Leu|Arg|Ala|Glu|Asp|Thr|Ala|Val|Tyr|
| | | |85| | | | |90| | | | |95| |
|Tyr|Cys|Ala|Lys|Leu|Ser|Arg|Ala|Gly|Gly|Phe|Asp|Ile|Trp|Gly|Gln|
| | |100| | | | |105| | | |110| | | |
|Gly|Thr|Met|Val|Thr|Val|Ser|Ser|Ala|Ser|Thr|Lys|Gly|Pro|Ser|Val|
| |115| | | |120| | | | |125| | | | |
|Phe|Pro|Leu|Ala|Pro|Ser|Ser|Lys|Ser|Thr|Ser|Gly|Gly|Thr|Ala|Ala|
|130| | | | |135| | | | |140| | | | |
|Leu|Gly|Cys|Leu|Val|Lys|Asp|Tyr|Phe|Pro|Glu|Pro|Val|Thr|Val|Ser|
|145| | | |150| | | |155| | | | |160| |
|Trp|Asn|Ser|Gly|Ala|Leu|Thr|Ser|Gly|Val|His|Thr|Phe|Pro|Ala|Val|
| | | |165| | | |170| | | |175| | | |
|Leu|Gln|Ser|Ser|Gly|Leu|Tyr|Ser|Leu|Ser|Ser|Val|Val|Thr|Val|Pro|
| | |180| | | |185| | | | |190| | | |
|Ser|Ser|Ser|Leu|Gly|Thr|Gln|Thr|Tyr|Ile|Cys|Asn|Val|Asn|His|Lys|
| |195| | | |200| | | | |205| | | | |
|Pro|Ser|Asn|Thr|Lys|Val|Asp|Lys|Lys|Ala|Glu|Pro|Lys|Ser|Cys|Asp|
|210| | | |215| | | | |220| | | | | |
|Lys|Thr|Ser|His|His|His|His|His|His| | | | | | | |
|225| | | |230| | | | | | | | | | | |

( 2 ) INFORMATION FOR SEQ ID NO:3:

( i ) SEQUENCE CHARACTERISTICS:
        ( A ) LENGTH: 732 base pairs
        ( B ) TYPE: nucleic acid
        ( C ) STRANDEDNESS: double
        ( D ) TOPOLOGY: circular ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens
        ( F ) TISSUE TYPE: Gut-associated lymphoid
        ( G ) CELL TYPE: Lymphocyte ( v i i ) IMMEDIATE SOURCE:
        ( B ) CLONE: 5-4

( i x ) FEATURE:
        ( A ) NAME/KEY: CDS
        ( B ) LOCATION: 1..732
        ( D ) OTHER INFORMATION: /codon_start= 1
            / product= "Human Heavy Chain of IgG ANCA
            associated with UC"

( i x ) FEATURE:
        ( A ) NAME/KEY: misc_RNA
        ( B ) LOCATION: 1..15
        ( D ) OTHER INFORMATION: /product="N-Terminal Tag"

( i x ) FEATURE:
      ( A ) NAME/KEY: misc_RNA
      ( B ) LOCATION: 16..93
      ( D ) OTHER INFORMATION: /label=FR1
          / note= ""FR1"refers to Framework Region 1"

( i x ) FEATURE:
      ( A ) NAME/KEY: misc_RNA
      ( B ) LOCATION: 94..108
      ( D ) OTHER INFORMATION: /label=CDR1
          / note= ""CDR1"refers to Complimentarity
          Determining Region 1"

( i x ) FEATURE:
      ( A ) NAME/KEY: misc_RNA
      ( B ) LOCATION: 109..150
      ( D ) OTHER INFORMATION: /label=FR2
          / note= ""FR2"refers to Framework Region 2"

( i x ) FEATURE:
      ( A ) NAME/KEY: misc_RNA
      ( B ) LOCATION: 151..201
      ( D ) OTHER INFORMATION: /label=CDR2
          / note= ""CDR2"refers to Complimentarity
          Determining Region 2"

( i x ) FEATURE:
      ( A ) NAME/KEY: misc_RNA
      ( B ) LOCATION: 202..297
      ( D ) OTHER INFORMATION: /label=FR3
          / note= ""FR3"refers to Framework Region 3"

( i x ) FEATURE:
      ( A ) NAME/KEY: misc_RNA
      ( B ) LOCATION: 298..360
      ( D ) OTHER INFORMATION: /label=CDR3
          / note= ""CDR3"refers to Complimentarity
          Determining Region 3"

( i x ) FEATURE:
      ( A ) NAME/KEY: misc_RNA
      ( B ) LOCATION: 361..393
      ( D ) OTHER INFORMATION: /label=FR4
          / note= ""FR4"refers to Framework Region 4"

( i x ) FEATURE:
      ( A ) NAME/KEY: misc_RNA
      ( B ) LOCATION: 394..684
      ( D ) OTHER INFORMATION: /label=CH1
          / note= ""CH1"refers to Constant Segment of the
          Heavy Chain"

( i x ) FEATURE:
      ( A ) NAME/KEY: misc_RNA
      ( B ) LOCATION: 685..711
      ( D ) OTHER INFORMATION: /label=Hinge
          / note= ""Hinge"refers to Partial Hinge Segment of
          the Heavy Chain"

( i x ) FEATURE:
      ( A ) NAME/KEY: misc_RNA
      ( B ) LOCATION: 712..732
      ( D ) OTHER INFORMATION: /label=Hex-HTag
          / note= ""Hex-HTag"refers to Hexahistidine Tag"

( i x ) FEATURE:
      ( A ) NAME/KEY: misc_RNA
      ( B ) LOCATION: 16..684
      ( D ) OTHER INFORMATION: /label=Fd
          / note= ""Fd"refers to the Fd of the Heavy Chain"

( i x ) FEATURE:
      ( A ) NAME/KEY: misc_RNA
      ( B ) LOCATION: 16..297
      ( D ) OTHER INFORMATION: /label=VHSEGMENT
          / note= ""VHSEGMENT"refers to Variable Segment of
          the Heavy Chain"

( i x ) FEATURE:
      ( A ) NAME/KEY: misc_RNA (B) LOCATION: 298..363
(D) OTHER INFORMATION: /label=D
/ note= ""D"refers to Diversity Segment"

(ix) FEATURE:
(A) NAME/KEY: misc_RNA
(B) LOCATION: 364..408
(D) OTHER INFORMATION: /label=JH
/ note= ""JH"refers to Joining Segment of the Heavy Chain"

(ix) FEATURE:
(A) NAME/KEY: misc_RNA
(B) LOCATION: 16..408
(D) OTHER INFORMATION: /label=VHDOMAIN
/ note= ""VHDOMAIN"refers to Variable Domain of the Heavy Chain"

(xi) SEQUENCE DESCRIPTION: SEQ ID NO:3:

| | | | | | | | | | | | | | | | | |
|---|---|---|---|---|---|---|---|---|---|---|---|---|---|---|---|---|
| CTC | GAG | TCT | GGG | GGA | GGC | GTG | GTC | CAG | CCT | GGG | AAG | TCC | CTG | AGA | CTC | 48 |
| Leu | Glu | Ser | Gly | Gly | Gly | Val | Val | Gln | Pro | Gly | Lys | Ser | Leu | Arg | Leu | |
| 1 | | | | 5 | | | | | 10 | | | | | 15 | | |
| TCC | TGT | GCA | GCC | TCT | GGA | TTC | ACC | TTC | AGG | AAC | TAT | GGC | ATG | CAC | TGG | 96 |
| Ser | Cys | Ala | Ala | Ser | Gly | Phe | Thr | Phe | Arg | Asn | Tyr | Gly | Met | His | Trp | |
| | | | 20 | | | | | 25 | | | | | 30 | | | |
| GTC | CGG | CAG | GCT | CCA | GGC | AAG | GGG | CTG | GAG | TGG | GTG | GCA | GGT | ATT | TCC | 144 |
| Val | Arg | Gln | Ala | Pro | Gly | Lys | Gly | Leu | Glu | Trp | Val | Ala | Gly | Ile | Ser | |
| | | 35 | | | | | 40 | | | | | 45 | | | | |
| TCT | GAT | GGA | AGA | AAA | AAA | AAG | TAT | GTA | GAC | TCC | GTG | AAG | GGC | CGA | TTC | 192 |
| Ser | Asp | Gly | Arg | Lys | Lys | Lys | Tyr | Val | Asp | Ser | Val | Lys | Gly | Arg | Phe | |
| | 50 | | | | | 55 | | | | | 60 | | | | | |
| TTC | ATC | TCC | AGA | GAC | AAT | TCC | AAG | AAC | ACC | CTG | TAT | CTG | CAA | TTG | AAC | 240 |
| Phe | Ile | Ser | Arg | Asp | Asn | Ser | Lys | Asn | Thr | Leu | Tyr | Leu | Gln | Leu | Asn | |
| 65 | | | | | 70 | | | | | 75 | | | | | 80 | |
| AGC | CTG | AGA | GCT | GAG | GAC | ACG | GCT | GTC | TAT | TAC | TGT | GCG | AAA | GAT | GAG | 288 |
| Ser | Leu | Arg | Ala | Glu | Asp | Thr | Ala | Val | Tyr | Tyr | Cys | Ala | Lys | Asp | Glu | |
| | | | | 85 | | | | | 90 | | | | | 95 | | |
| TTT | AGT | TCT | ACC | CGG | AAG | AAC | TTC | TTG | ACT | GGT | CAA | TCA | AAG | ACC | TTT | 336 |
| Phe | Ser | Ser | Thr | Arg | Lys | Asn | Phe | Leu | Thr | Gly | Gln | Ser | Lys | Thr | Phe | |
| | | | 100 | | | | | 105 | | | | | 110 | | | |
| GCG | GCC | TAC | TAC | GGT | ATG | GAC | GTC | TGG | GGC | CAA | GGG | ACC | ACG | GTC | ACC | 384 |
| Ala | Ala | Tyr | Tyr | Gly | Met | Asp | Val | Trp | Gly | Gln | Gly | Thr | Thr | Val | Thr | |
| | | 115 | | | | | 120 | | | | | 125 | | | | |
| GTC | TCC | TCA | GCC | TCC | ACC | AAG | GGC | CCA | TCG | GTC | TTC | CCC | CTG | GCA | CCC | 432 |
| Val | Ser | Ser | Ala | Ser | Thr | Lys | Gly | Pro | Ser | Val | Phe | Pro | Leu | Ala | Pro | |
| | 130 | | | | | 135 | | | | | 140 | | | | | |
| TCC | TCC | AAG | AGC | ACC | TCT | GGG | GGC | ACA | GCG | GCC | CTG | GGC | TGC | CTG | GTC | 480 |
| Ser | Ser | Lys | Ser | Thr | Ser | Gly | Gly | Thr | Ala | Ala | Leu | Gly | Cys | Leu | Val | |
| 145 | | | | | 150 | | | | | 155 | | | | | 160 | |
| AAG | GAC | TAC | TTC | CCC | GAA | CCG | GTG | ACG | GTG | TCG | TGG | AAC | TCA | GGC | GCC | 528 |
| Lys | Asp | Tyr | Phe | Pro | Glu | Pro | Val | Thr | Val | Ser | Trp | Asn | Ser | Gly | Ala | |
| | | | | 165 | | | | | 170 | | | | | 175 | | |
| CTG | ACC | AGC | GGC | GTG | CAC | ACC | TTC | CCG | GCT | GTC | CTA | CAG | TCC | TCA | GGA | 576 |
| Leu | Thr | Ser | Gly | Val | His | Thr | Phe | Pro | Ala | Val | Leu | Gln | Ser | Ser | Gly | |
| | | | 180 | | | | | 185 | | | | | 190 | | | |
| CTC | TAC | TCC | CTC | AGC | AGC | GTG | GTG | ACC | GTG | CCC | TCC | AGC | AGC | TTG | GGC | 624 |
| Leu | Tyr | Ser | Leu | Ser | Ser | Val | Val | Thr | Val | Pro | Ser | Ser | Ser | Leu | Gly | |
| | | 195 | | | | | 200 | | | | | 205 | | | | |
| ACC | CAG | ACC | TAC | ATC | TGC | AAC | GTG | AAT | CAC | AAG | CCC | AGC | AAC | ACC | AAG | 672 |
| Thr | Gln | Thr | Tyr | Ile | Cys | Asn | Val | Asn | His | Lys | Pro | Ser | Asn | Thr | Lys | |
| | 210 | | | | | 215 | | | | | 220 | | | | | |
| GTG | GAC | AAG | AAA | GCA | GAG | CCC | AAA | TCT | TGT | GAC | AAA | ACT | AGT | CAC | CAC | 720 |
| Val | Asp | Lys | Lys | Ala | Glu | Pro | Lys | Ser | Cys | Asp | Lys | Thr | Ser | His | His | |
| 225 | | | | | 230 | | | | | 235 | | | | | 240 | |

```
C A C   C A C   C A C   C A C                                                                                       7 3 2
H i s   H i s   H i s   H i s
```

( 2 ) INFORMATION FOR SEQ ID NO:4:

( i ) SEQUENCE CHARACTERISTICS:
        ( A ) LENGTH: 244 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Leu  Glu  Ser  Gly  Gly  Gly  Val  Val  Gln  Pro  Gly  Lys  Ser  Leu  Arg  Leu
 1                    5                        10                       15

Ser  Cys  Ala  Ala  Ser  Gly  Phe  Thr  Phe  Arg  Asn  Tyr  Gly  Met  His  Trp
               20                        25                       30

Val  Arg  Gln  Ala  Pro  Gly  Lys  Gly  Leu  Glu  Trp  Val  Ala  Gly  Ile  Ser
          35                        40                       45

Ser  Asp  Gly  Arg  Lys  Lys  Tyr  Val  Asp  Ser  Val  Lys  Gly  Arg  Phe
     50                       55                       60

Phe  Ile  Ser  Arg  Asp  Asn  Ser  Lys  Asn  Thr  Leu  Tyr  Leu  Gln  Leu  Asn
 65                      70                       75                       80

Ser  Leu  Arg  Ala  Glu  Asp  Thr  Ala  Val  Tyr  Tyr  Cys  Ala  Lys  Asp  Glu
               85                        90                       95

Phe  Ser  Ser  Thr  Arg  Lys  Asn  Phe  Leu  Thr  Gly  Gln  Ser  Lys  Thr  Phe
               100                       105                      110

Ala  Ala  Tyr  Tyr  Gly  Met  Asp  Val  Trp  Gly  Gln  Gly  Thr  Thr  Val  Thr
               115                       120                      125

Val  Ser  Ser  Ala  Ser  Thr  Lys  Gly  Pro  Ser  Val  Phe  Pro  Leu  Ala  Pro
     130                      135                      140

Ser  Ser  Lys  Ser  Thr  Ser  Gly  Gly  Thr  Ala  Ala  Leu  Gly  Cys  Leu  Val
145                      150                      155                      160

Lys  Asp  Tyr  Phe  Pro  Glu  Pro  Val  Thr  Val  Ser  Trp  Asn  Ser  Gly  Ala
               165                       170                      175

Leu  Thr  Ser  Gly  Val  His  Thr  Phe  Pro  Ala  Val  Leu  Gln  Ser  Ser  Gly
               180                       185                      190

Leu  Tyr  Ser  Leu  Ser  Ser  Val  Val  Thr  Val  Pro  Ser  Ser  Ser  Leu  Gly
          195                      200                      205

Thr  Gln  Thr  Tyr  Ile  Cys  Asn  Val  Asn  His  Lys  Pro  Ser  Asn  Thr  Lys
     210                      215                      220

Val  Asp  Lys  Lys  Ala  Glu  Pro  Lys  Ser  Cys  Asp  Lys  Thr  Ser  His  His
225                      230                      235                      240

His  His  His  His
```

( 2 ) INFORMATION FOR SEQ ID NO:5:

( i ) SEQUENCE CHARACTERISTICS:
        ( A ) LENGTH: 642 base pairs
        ( B ) TYPE: nucleic acid
        ( C ) STRANDEDNESS: double
        ( D ) TOPOLOGY: circular ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: Gut-associated lymphoid ( G ) CELL TYPE: Lymphocyte ( v i i ) IMMEDIATE SOURCE:
    ( B ) CLONE: 5-3

( i x ) FEATURE:
    ( A ) NAME/KEY: CDS
    ( B ) LOCATION: 1..642
    ( D ) OTHER INFORMATION: /codon_start= 1
        / product= "Kappa Light Chain of ANCA associated
        with Ulcerative Colitis"

( i x ) FEATURE:
    ( A ) NAME/KEY: misc_RNA
    ( B ) LOCATION: 1..3
    ( D ) OTHER INFORMATION: /label= N- TerminalTag ( i x ) FEATURE:
    ( A ) NAME/KEY: misc_RNA
    ( B ) LOCATION: 4..285
    ( D ) OTHER INFORMATION: /label=VKSEGMENT
        / note= ""VKSEGMENT"refers to Variable Segment of
        the Kappa Light Chain"

( i x ) FEATURE:
    ( A ) NAME/KEY: misc_RNA
    ( B ) LOCATION: 286..324
    ( D ) OTHER INFORMATION: /label=JK
        / note= ""JK"refers to Joining Segment of the
        Kappa Light Chain"

( i x ) FEATURE:
    ( A ) NAME/KEY: misc_RNA
    ( B ) LOCATION: 325..642
    ( D ) OTHER INFORMATION: /label=CK
        / note= ""CK"refers to Constant Segment of the
        Kappa Light Chain"

( i x ) FEATURE:
    ( A ) NAME/KEY: misc_RNA
    ( B ) LOCATION: 4..66
    ( D ) OTHER INFORMATION: /label=FR1
        / note= ""FR1"refers to Framework Region 1"

( i x ) FEATURE:
    ( A ) NAME/KEY: misc_RNA
    ( B ) LOCATION: 67..102
    ( D ) OTHER INFORMATION: /label=CDR1
        / note= ""CDR1"refers to Complimentarity
        Determining Region 1"

( i x ) FEATURE:
    ( A ) NAME/KEY: misc_RNA
    ( B ) LOCATION: 103..147
    ( D ) OTHER INFORMATION: /label=FR2
        / note= ""FR2"refers to Framework Region 2"

( i x ) FEATURE:
    ( A ) NAME/KEY: misc_RNA
    ( B ) LOCATION: 148..168
    ( D ) OTHER INFORMATION: /label=CDR2
        / note= ""CDR2"refers to Complimentarity
        Determining Region 2"

( i x ) FEATURE:
    ( A ) NAME/KEY: misc_RNA
    ( B ) LOCATION: 169..264
    ( D ) OTHER INFORMATION: /label=FR3
        / note= ""FR3"refers to Framework Region 3"

( i x ) FEATURE:
    ( A ) NAME/KEY: misc_RNA
    ( B ) LOCATION: 265..291
    ( D ) OTHER INFORMATION: /label=CDR3
        / note= ""CDR3"refers to Complimentarity
        Determining Region 3"

( i x ) FEATURE:
    ( A ) NAME/KEY: misc_RNA
    ( B ) LOCATION: 292..324

( D ) OTHER INFORMATION: /label=FR4
/ note= ""FR4"refers to Framework Region 4"

( x i ) SEQUENCE DESCRIPTION: SEQ ID NO:5:

| GCC | GAG | CTC | ACG | CAG | TCT | CCA | GGC | ACC | CTG | TCT | TTG | TTT | CCA | GGG | GAA | 48 |
|---|---|---|---|---|---|---|---|---|---|---|---|---|---|---|---|---|
| Ala | Glu | Leu | Thr | Gln | Ser | Pro | Gly | Thr | Leu | Ser | Leu | Phe | Pro | Gly | Glu | |
| 1 | | | | 5 | | | | | 10 | | | | | 15 | | |

| AGA | GCC | ACT | CTC | TCC | TGC | AGG | GCC | AGT | CAG | AGA | ATT | AGC | ACC | AGT | TTC | 96 |
|---|---|---|---|---|---|---|---|---|---|---|---|---|---|---|---|---|
| Arg | Ala | Thr | Leu | Ser | Cys | Arg | Ala | Ser | Gln | Arg | Ile | Ser | Thr | Ser | Phe | |
| | | | 20 | | | | | 25 | | | | | 30 | | | |

| TTA | GCC | TGG | TAC | CAG | CAG | AAG | CCT | GGC | CAG | TCT | CCC | AGG | CTC | CTC | ATC | 144 |
|---|---|---|---|---|---|---|---|---|---|---|---|---|---|---|---|---|
| Leu | Ala | Trp | Tyr | Gln | Gln | Lys | Pro | Gly | Gln | Ser | Pro | Arg | Leu | Leu | Ile | |
| | | | 35 | | | | | 40 | | | | | 45 | | | |

| TTT | GAT | GCA | TCC | ACC | AGG | GCC | CCT | GGC | ATC | CCT | GAC | AGG | TTC | AGT | GCC | 192 |
|---|---|---|---|---|---|---|---|---|---|---|---|---|---|---|---|---|
| Phe | Asp | Ala | Ser | Thr | Arg | Ala | Pro | Gly | Ile | Pro | Asp | Arg | Phe | Ser | Ala | |
| | 50 | | | | | 55 | | | | | 60 | | | | | |

| AGT | TGG | TCT | GGG | ACA | GAC | TTC | ACT | CTC | ACC | ATC | AGC | AGA | CTG | GAG | CCT | 240 |
|---|---|---|---|---|---|---|---|---|---|---|---|---|---|---|---|---|
| Ser | Trp | Ser | Gly | Thr | Asp | Phe | Thr | Leu | Thr | Ile | Ser | Arg | Leu | Glu | Pro | |
| 65 | | | | | 70 | | | | | 75 | | | | | 80 | |

| GAA | GAT | TTT | GCA | GTC | TAT | TAC | TGT | CAA | CAT | TAT | GGT | GGG | TCT | CCC | TGG | 288 |
|---|---|---|---|---|---|---|---|---|---|---|---|---|---|---|---|---|
| Glu | Asp | Phe | Ala | Val | Tyr | Tyr | Cys | Gln | His | Tyr | Gly | Gly | Ser | Pro | Trp | |
| | | | | 85 | | | | | 90 | | | | | 95 | | |

| ACG | TTC | GGC | CAA | GGG | ACC | AAG | GTG | GAA | ATC | AAG | CGA | ACT | GTG | GCT | GCA | 336 |
|---|---|---|---|---|---|---|---|---|---|---|---|---|---|---|---|---|
| Thr | Phe | Gly | Gln | Gly | Thr | Lys | Val | Glu | Ile | Lys | Arg | Thr | Val | Ala | Ala | |
| | | | 100 | | | | | 105 | | | | | 110 | | | |

| CCA | TCT | GTC | TTC | ATC | TTC | CCG | CCA | TCT | GAT | GAG | CAG | TTG | AAA | TCT | GGA | 384 |
|---|---|---|---|---|---|---|---|---|---|---|---|---|---|---|---|---|
| Pro | Ser | Val | Phe | Ile | Phe | Pro | Pro | Ser | Asp | Glu | Gln | Leu | Lys | Ser | Gly | |
| | | 115 | | | | | 120 | | | | | 125 | | | | |

| ACT | GCC | TCT | GTT | GTG | TGC | CTG | CTG | AAT | AAC | TTC | TAT | CCC | AGA | GAG | GCC | 432 |
|---|---|---|---|---|---|---|---|---|---|---|---|---|---|---|---|---|
| Thr | Ala | Ser | Val | Val | Cys | Leu | Leu | Asn | Asn | Phe | Tyr | Pro | Arg | Glu | Ala | |
| | 130 | | | | | 135 | | | | | 140 | | | | | |

| AAA | GTA | CAG | TGG | AAG | GTG | GAT | AAC | GCC | CTC | CAA | TCG | GGT | AAC | TCC | CAG | 480 |
|---|---|---|---|---|---|---|---|---|---|---|---|---|---|---|---|---|
| Lys | Val | Gln | Trp | Lys | Val | Asp | Asn | Ala | Leu | Gln | Ser | Gly | Asn | Ser | Gln | |
| 145 | | | | | 150 | | | | | 155 | | | | | 160 | |

| GAG | AGT | GTC | ACA | GAG | CAG | GAC | AGC | AAG | GAC | AGC | ACC | TAC | AGC | CTC | AGC | 528 |
|---|---|---|---|---|---|---|---|---|---|---|---|---|---|---|---|---|
| Glu | Ser | Val | Thr | Glu | Gln | Asp | Ser | Lys | Asp | Ser | Thr | Tyr | Ser | Leu | Ser | |
| | | | | 165 | | | | | 170 | | | | | 175 | | |

| AGC | ACC | CTG | ACG | CTG | AGC | AAA | GCA | GAC | TAC | GAG | AAA | CAC | AAA | GTC | TAC | 576 |
|---|---|---|---|---|---|---|---|---|---|---|---|---|---|---|---|---|
| Ser | Thr | Leu | Thr | Leu | Ser | Lys | Ala | Asp | Tyr | Glu | Lys | His | Lys | Val | Tyr | |
| | | | 180 | | | | | 185 | | | | | 190 | | | |

| GCC | TGC | GAA | GTC | ACC | CAT | CAG | GGC | CTG | AGC | TCG | CCC | GTC | ACA | AAG | AGC | 624 |
|---|---|---|---|---|---|---|---|---|---|---|---|---|---|---|---|---|
| Ala | Cys | Glu | Val | Thr | His | Gln | Gly | Leu | Ser | Ser | Pro | Val | Thr | Lys | Ser | |
| | | 195 | | | | | 200 | | | | | 205 | | | | |

| TTC | AAC | AGG | GGA | GAG | TGT | | | | | | | | | | | 642 |
|---|---|---|---|---|---|---|---|---|---|---|---|---|---|---|---|---|
| Phe | Asn | Arg | Gly | Glu | Cys | | | | | | | | | | | |
| | | 210 | | | | | | | | | | | | | | |

( 2 ) INFORMATION FOR SEQ ID NO:6:

( i ) SEQUENCE CHARACTERISTICS:
( A ) LENGTH: 214 amino acids
( B ) TYPE: amino acid
( D ) TOPOLOGY: linear ( i i ) MOLECULE TYPE: protein ( x i ) SEQUENCE DESCRIPTION: SEQ ID NO:6:

| Ala | Glu | Leu | Thr | Gln | Ser | Pro | Gly | Thr | Leu | Ser | Leu | Phe | Pro | Gly | Glu |
|---|---|---|---|---|---|---|---|---|---|---|---|---|---|---|---|
| 1 | | | | 5 | | | | | 10 | | | | | 15 | |

| Arg | Ala | Thr | Leu | Ser | Cys | Arg | Ala | Ser | Gln | Arg | Ile | Ser | Thr | Ser | Phe |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Gln | Ser | Pro | Arg | Leu | Leu | Ile |
|---|---|---|---|---|---|---|---|---|---|---|---|---|---|---|---|

|     |     |     |     | 35  |     |     |     |     | 40  |     |     |     |     | 45  |     |
| --- | --- | --- | --- | --- | --- | --- | --- | --- | --- | --- | --- | --- | --- | --- | --- |
| Phe | Asp | Ala | Ser | Thr | Arg | Ala | Pro | Gly | Ile | Pro | Asp | Arg | Phe | Ser | Ala |
|     | 50  |     |     |     |     | 55  |     |     |     |     | 60  |     |     |     |     |
| Ser | Trp | Ser | Gly | Thr | Asp | Phe | Thr | Leu | Thr | Ile | Ser | Arg | Leu | Glu | Pro |
| 65  |     |     |     |     | 70  |     |     |     |     | 75  |     |     |     |     | 80  |
| Glu | Asp | Phe | Ala | Val | Tyr | Tyr | Cys | Gln | His | Tyr | Gly | Gly | Ser | Pro | Trp |
|     |     |     |     | 85  |     |     |     |     | 90  |     |     |     |     | 95  |     |
| Thr | Phe | Gly | Gln | Gly | Thr | Lys | Val | Glu | Ile | Lys | Arg | Thr | Val | Ala | Ala |
|     |     |     | 100 |     |     |     |     | 105 |     |     |     |     | 110 |     |     |
| Pro | Ser | Val | Phe | Ile | Phe | Pro | Pro | Ser | Asp | Glu | Gln | Leu | Lys | Ser | Gly |
|     |     | 115 |     |     |     |     | 120 |     |     |     |     | 125 |     |     |     |
| Thr | Ala | Ser | Val | Val | Cys | Leu | Leu | Asn | Asn | Phe | Tyr | Pro | Arg | Glu | Ala |
|     | 130 |     |     |     |     | 135 |     |     |     |     | 140 |     |     |     |     |
| Lys | Val | Gln | Trp | Lys | Val | Asp | Asn | Ala | Leu | Gln | Ser | Gly | Asn | Ser | Gln |
| 145 |     |     |     |     | 150 |     |     |     |     | 155 |     |     |     |     | 160 |
| Glu | Ser | Val | Thr | Glu | Gln | Asp | Ser | Lys | Asp | Ser | Thr | Tyr | Ser | Leu | Ser |
|     |     |     |     | 165 |     |     |     |     | 170 |     |     |     |     | 175 |     |
| Ser | Thr | Leu | Thr | Leu | Ser | Lys | Ala | Asp | Tyr | Glu | Lys | His | Lys | Val | Tyr |
|     |     |     | 180 |     |     |     |     | 185 |     |     |     |     | 190 |     |     |
| Ala | Cys | Glu | Val | Thr | His | Gln | Gly | Leu | Ser | Ser | Pro | Val | Thr | Lys | Ser |
|     |     | 195 |     |     |     |     | 200 |     |     |     |     | 205 |     |     |     |
| Phe | Asn | Arg | Gly | Glu | Cys |
|     | 210 |     |     |     |     |

(2) INFORMATION FOR SEQ ID NO:7:

( i ) SEQUENCE CHARACTERISTICS:
        ( A ) LENGTH: 645 base pairs
        ( B ) TYPE: nucleic acid
        ( C ) STRANDEDNESS: double
        ( D ) TOPOLOGY: circular ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens
        ( F ) TISSUE TYPE: Gut-associated lymphoid
        ( G ) CELL TYPE: Lymphocyte ( v i i ) IMMEDIATE SOURCE:
        ( B ) CLONE: 5-4

( i x ) FEATURE:
        ( A ) NAME/KEY: CDS
        ( B ) LOCATION: 1..645
        ( D ) OTHER INFORMATION: /codon_start= 1
            / product= "Kappa Light Chain of ANCA associated
            with Ulcerative Colitis"

( i x ) FEATURE:
        ( A ) NAME/KEY: misc_RNA
        ( B ) LOCATION: 1..3
        ( D ) OTHER INFORMATION: /label= N- TerminalTag ( i x ) FEATURE:
        ( A ) NAME/KEY: misc_RNA
        ( B ) LOCATION: 4..285
        ( D ) OTHER INFORMATION: /label=VKSEGMENT
            / note= ""VKSEGMENT"refers to Variable Segment of
            the Kappa Light Chain"

( i x ) FEATURE:
        ( A ) NAME/KEY: misc_RNA
        ( B ) LOCATION: 286..327

(D) OTHER INFORMATION: /label=JK
/ note= ""JK"refers to Joining Segment of the
Kappa Light Chain"

(ix) FEATURE:
(A) NAME/KEY: misc_RNA
(B) LOCATION: 328..645
(D) OTHER INFORMATION: /label=CK
/ note= ""CK"refers to Constant Segment of the
Kappa Light Chain"

(ix) FEATURE:
(A) NAME/KEY: misc_RNA
(B) LOCATION: 4..66
(D) OTHER INFORMATION: /label=FR1
/ note= ""FR1"refers to Framework Region 1"

(ix) FEATURE:
(A) NAME/KEY: misc_RNA
(B) LOCATION: 67..102
(D) OTHER INFORMATION: /label=CDR1
/ note= ""CDR1"refers to Complimentarity
Determining Region 1"

(ix) FEATURE:
(A) NAME/KEY: misc_RNA
(B) LOCATION: 103..147
(D) OTHER INFORMATION: /label=FR2
/ note= ""FR2"refers to Framework Region 2"

(ix) FEATURE:
(A) NAME/KEY: misc_RNA
(B) LOCATION: 148..168
(D) OTHER INFORMATION: /label=CDR2
/ note= ""CDR2"refers to Complimentarity
Determining Region 2"

(ix) FEATURE:
(A) NAME/KEY: misc_RNA
(B) LOCATION: 169..264
(D) OTHER INFORMATION: /label=FR3
/ note= ""FR3"refers to Framework Region 3"

(ix) FEATURE:
(A) NAME/KEY: misc_RNA
(B) LOCATION: 265..294
(D) OTHER INFORMATION: /label=CDR3
/ note= ""CDR3"refers to Complimentarity
Determining Region 3"

(ix) FEATURE:
(A) NAME/KEY: misc_RNA
(B) LOCATION: 295..327
(D) OTHER INFORMATION: /label=FR4
/ note= ""FR4"refers to Framework Region 4"

(xi) SEQUENCE DESCRIPTION: SEQ ID NO:7:

| GCC | GAG | CTC | ACG | CAG | TCT | CCA | GGC | ACC | CTG | TCT | TTG | TCT | CCA | GGG | GAA | 48 |
|---|---|---|---|---|---|---|---|---|---|---|---|---|---|---|---|---|
| Ala | Glu | Leu | Thr | Gln | Ser | Pro | Gly | Thr | Leu | Ser | Leu | Ser | Pro | Gly | Glu | |
| 1 | | | | 5 | | | | | 10 | | | | | 15 | | |

| AGA | GCC | ACC | CTC | TCC | TGC | AGG | GCC | AGT | CAG | GGT | GTT | AGC | AGC | GGC | TCC | 96 |
|---|---|---|---|---|---|---|---|---|---|---|---|---|---|---|---|---|
| Arg | Ala | Thr | Leu | Ser | Cys | Arg | Ala | Ser | Gln | Gly | Val | Ser | Ser | Gly | Ser | |
| | | | 20 | | | | | 25 | | | | | 30 | | | |

| TTA | GCC | TGG | TAT | CAG | CAG | AAA | GCT | GGC | CAG | GCT | CCC | AGG | CTC | CTC | ATC | 144 |
|---|---|---|---|---|---|---|---|---|---|---|---|---|---|---|---|---|
| Leu | Ala | Trp | Tyr | Gln | Gln | Lys | Ala | Gly | Gln | Ala | Pro | Arg | Leu | Leu | Ile | |
| | | 35 | | | | | 40 | | | | | 45 | | | | |

| TAT | GGT | GCA | TCC | AGG | AGG | GCC | ACT | GGC | ATC | CCA | GAC | AGG | TTC | ACT | GGC | 192 |
|---|---|---|---|---|---|---|---|---|---|---|---|---|---|---|---|---|
| Tyr | Gly | Ala | Ser | Arg | Arg | Ala | Thr | Gly | Ile | Pro | Asp | Arg | Phe | Thr | Gly | |
| | 50 | | | | | 55 | | | | | 60 | | | | | |

| AGT | GGG | TCT | GGG | ACA | GAC | TTC | ACT | CTC | ACC | ATC | ACC | AGA | CTG | GAG | CCT | 240 |
|---|---|---|---|---|---|---|---|---|---|---|---|---|---|---|---|---|
| Ser | Gly | Ser | Gly | Thr | Asp | Phe | Thr | Leu | Thr | Ile | Thr | Arg | Leu | Glu | Pro | |
| 65 | | | | | 70 | | | | | 75 | | | | | 80 | |

| GAA | GAT | TTT | GCA | GTG | TAT | TAC | TGT | CAG | CAG | TAT | GGT | AGC | TCC | CAG | GGA | 288 |
|---|---|---|---|---|---|---|---|---|---|---|---|---|---|---|---|---|
| Glu | Asp | Phe | Ala | Val | Tyr | Tyr | Cys | Gln | Gln | Tyr | Gly | Ser | Ser | Gln | Gly | |

|  |  |  |  |  |  |  |  |  |  |  |  |  |  |  |  |
|---|---|---|---|---|---|---|---|---|---|---|---|---|---|---|---|
|  |  |  |  | 85 |  |  |  |  | 90 |  |  |  |  | 95 |  |
| TTC | ACT | TTC | GGC | CCT | GGG | ACC | AAA | GTG | GAT | CTC | AAA | CGA | ACT | GTG | GCT | 336 |
| Phe | Thr | Phe | Gly | Pro | Gly | Thr | Lys | Val | Asp | Leu | Lys | Arg | Thr | Val | Ala |
|  |  |  | 100 |  |  |  | 105 |  |  |  |  |  | 110 |  |  |
| GCA | CCA | TCT | GTC | TTC | ATC | TTC | CCG | CCA | TCT | GAT | GAG | CAG | TTG | AAA | TCT | 384 |
| Ala | Pro | Ser | Val | Phe | Ile | Phe | Pro | Pro | Ser | Asp | Glu | Gln | Leu | Lys | Ser |
|  |  | 115 |  |  |  |  | 120 |  |  |  |  | 125 |  |  |  |
| GGA | ACT | GCC | TCT | GTT | GTG | TGC | CTG | CTG | AAT | AAC | TTC | TAT | CCC | AGA | GAG | 432 |
| Gly | Thr | Ala | Ser | Val | Val | Cys | Leu | Leu | Asn | Asn | Phe | Tyr | Pro | Arg | Glu |
|  | 130 |  |  |  |  | 135 |  |  |  |  | 140 |  |  |  |  |
| GCC | AAA | GTA | CAG | TGG | AAG | GTG | GAT | AAC | GCC | CTC | CAA | TCG | GGT | AAC | TCC | 480 |
| Ala | Lys | Val | Gln | Trp | Lys | Val | Asp | Asn | Ala | Leu | Gln | Ser | Gly | Asn | Ser |
| 145 |  |  |  |  | 150 |  |  |  |  | 155 |  |  |  |  | 160 |
| CAG | GAG | AGT | GTC | ACA | GAG | CAG | GAC | AGC | AAG | GAC | AGC | ACC | TAC | AGC | CTC | 528 |
| Gln | Glu | Ser | Val | Thr | Glu | Gln | Asp | Ser | Lys | Asp | Ser | Thr | Tyr | Ser | Leu |
|  |  |  |  | 165 |  |  |  |  | 170 |  |  |  |  | 175 |  |
| AGC | AGC | ACC | CTG | ACG | CTG | AGC | AAA | GCA | GAC | TAC | GAG | AAA | CAC | AAA | GTC | 576 |
| Ser | Ser | Thr | Leu | Thr | Leu | Ser | Lys | Ala | Asp | Tyr | Glu | Lys | His | Lys | Val |
|  |  |  | 180 |  |  |  |  | 185 |  |  |  |  | 190 |  |  |
| TAC | GCC | TGC | GAA | GTC | ACC | CAT | CAG | GGC | CTG | AGC | TCG | CCC | GTC | ACA | AAG | 624 |
| Tyr | Ala | Cys | Glu | Val | Thr | His | Gln | Gly | Leu | Ser | Ser | Pro | Val | Thr | Lys |
|  |  | 195 |  |  |  |  | 200 |  |  |  |  | 205 |  |  |  |
| AGC | TTC | AAC | AGG | GGA | GAG | TGT |  |  |  |  |  |  |  |  |  | 645 |
| Ser | Phe | Asn | Arg | Gly | Glu | Cys |
| 210 |  |  |  |  | 215 |  |

( 2 ) INFORMATION FOR SEQ ID NO:8:

( i ) SEQUENCE CHARACTERISTICS:
        ( A ) LENGTH: 215 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Ala | Glu | Leu | Thr | Gln | Ser | Pro | Gly | Thr | Leu | Ser | Leu | Ser | Pro | Gly | Glu |
|---|---|---|---|---|---|---|---|---|---|---|---|---|---|---|---|
| 1 |  |  |  | 5 |  |  |  |  | 10 |  |  |  |  | 15 |  |
| Arg | Ala | Thr | Leu | Ser | Cys | Arg | Ala | Ser | Gln | Gly | Val | Ser | Ser | Gly | Ser |
|  |  |  | 20 |  |  |  |  | 25 |  |  |  |  | 30 |  |  |
| Leu | Ala | Trp | Tyr | Gln | Gln | Lys | Ala | Gly | Gln | Ala | Pro | Arg | Leu | Leu | Ile |
|  |  | 35 |  |  |  |  | 40 |  |  |  |  | 45 |  |  |  |
| Tyr | Gly | Ala | Ser | Arg | Arg | Ala | Thr | Gly | Ile | Pro | Asp | Arg | Phe | Thr | Gly |
|  | 50 |  |  |  |  | 55 |  |  |  |  | 60 |  |  |  |  |
| Ser | Gly | Ser | Gly | Thr | Asp | Phe | Thr | Leu | Thr | Ile | Thr | Arg | Leu | Glu | Pro |
| 65 |  |  |  |  | 70 |  |  |  |  | 75 |  |  |  |  | 80 |
| Glu | Asp | Phe | Ala | Val | Tyr | Tyr | Cys | Gln | Gln | Tyr | Gly | Ser | Ser | Gln | Gly |
|  |  |  |  | 85 |  |  |  |  | 90 |  |  |  |  | 95 |  |
| Phe | Thr | Phe | Gly | Pro | Gly | Thr | Lys | Val | Asp | Leu | Lys | Arg | Thr | Val | Ala |
|  |  |  | 100 |  |  |  | 105 |  |  |  |  |  | 110 |  |  |
| Ala | Pro | Ser | Val | Phe | Ile | Phe | Pro | Pro | Ser | Asp | Glu | Gln | Leu | Lys | Ser |
|  |  | 115 |  |  |  |  | 120 |  |  |  |  | 125 |  |  |  |
| Gly | Thr | Ala | Ser | Val | Val | Cys | Leu | Leu | Asn | Asn | Phe | Tyr | Pro | Arg | Glu |
|  | 130 |  |  |  |  | 135 |  |  |  |  | 140 |  |  |  |  |
| Ala | Lys | Val | Gln | Trp | Lys | Val | Asp | Asn | Ala | Leu | Gln | Ser | Gly | Asn | Ser |
| 145 |  |  |  |  | 150 |  |  |  |  | 155 |  |  |  |  | 160 |
| Gln | Glu | Ser | Val | Thr | Glu | Gln | Asp | Ser | Lys | Asp | Ser | Thr | Tyr | Ser | Leu |
|  |  |  |  | 165 |  |  |  |  | 170 |  |  |  |  | 175 |  |
| Ser | Ser | Thr | Leu | Thr | Leu | Ser | Lys | Ala | Asp | Tyr | Glu | Lys | His | Lys | Val |

```
                    1 8 0                       1 8 5                         1 9 0
Tyr  Ala  Cys  Glu  Val  Thr  His  Gln  Gly  Leu  Ser  Ser  Pro  Val  Thr  Lys
          1 9 5                      2 0 0                    2 0 5

Ser  Phe  Asn  Arg  Gly  Glu  Cys
     2 1 0                 2 1 5
```

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_RNA
        ( B ) LOCATION: 1..30
        ( D ) OTHER INFORMATION: /label=CG1z
            / note= ""CG1z"refers to the cDNA Primer for IgG1
            Heavy Chain Constant Segments"

( x i ) SEQUENCE DESCRIPTION: SEQ ID NO:9:

```
GCATGTACTA  GTTTTGTCAC  AAGATTTGGG                                    30
```

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_RNA
        ( B ) LOCATION: 1..24
        ( D ) OTHER INFORMATION: /label=VH1a
            / note= ""VH1a"refers to the cDNA Primer for
            Variable Segments of the Heavy Chain that are
            Members of the VH1 Gene Family"

( x i ) SEQUENCE DESCRIPTION: SEQ ID NO:10:

```
CAGGTGCAGC  TCGAGCAGTC  TGGG                                          24
```

( 2 ) INFORMATION FOR SEQ ID NO:11:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_RNA
        ( B ) LOCATION: 1..24
        ( D ) OTHER INFORMATION: /label=VH3a / note= "VH3a"refers to the cDNA Primer for
Variable Segments of the Heavy Chain that are
Members of the VH3 Gene Family"

( x i ) SEQUENCE DESCRIPTION: SEQ ID NO:11:

GAGGTGCAGC TCGAGGAGTC TGGG                                   24

( 2 ) INFORMATION FOR SEQ ID NO:12:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_RNA
        ( B ) LOCATION: 1..23
        ( D ) OTHER INFORMATION: /label=VH2f
            / note= "VH2f"refers to the cDNA Primer for
            Variable Segments of the Heavy Chain that are
            Members of the VH2 Gene Family"

( x i ) SEQUENCE DESCRIPTION: SEQ ID NO:12:

CAGGTGCAGC TACTCGAGTC GGG                                    23

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_RNA
        ( B ) LOCATION: 1..24
        ( D ) OTHER INFORMATION: /label=VH3f
            / note= "VH3f"refers to the cDNA Primer for
            Variable Segments of the Heavy Chain that are
            Members of the VH3 Gene Family"

( x i ) SEQUENCE DESCRIPTION: SEQ ID NO:13:

GAGGTGCAGC TGCTCGAGTC TGGG                                   24

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: misc_RNA
        ( B ) LOCATION: 1..23

-continued ( D ) OTHER INFORMATION: /label=VH4f
                        / note= ""VH4f"refers to the cDNA Primer for
                        Variable Segments of the Heavy Chain that are
                        Members of the VH4 Gene Family"

( x i ) SEQUENCE DESCRIPTION: SEQ ID NO:14:

CAGGTGCAGC TGCTCGAGTC GGG                                                                           23

( 2 ) INFORMATION FOR SEQ ID NO:15:

( i ) SEQUENCE CHARACTERISTICS:
                ( A ) LENGTH: 23 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( i x ) FEATURE:
                ( A ) NAME/KEY: misc_RNA
                ( B ) LOCATION: 1..23
                ( D ) OTHER INFORMATION: /label=VH6a
                        / note= ""VH6a"refers to the cDNA Primer for
                        Variable Segments of the Heavy Chain that are
                        Members of the VH6 Gene Family"

( x i ) SEQUENCE DESCRIPTION: SEQ ID NO:15:

CAGGTACAGC TCGAGCAGTC AGG                                                                           23

( 2 ) INFORMATION FOR SEQ ID NO:16:

( i ) SEQUENCE CHARACTERISTICS:
                ( A ) LENGTH: 27 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( i x ) FEATURE:
                ( A ) NAME/KEY: misc_RNA
                ( B ) LOCATION: 1..27
                ( D ) OTHER INFORMATION: /label=VH6f
                        / note= ""VH6f"refers to the cDNA Primer for
                        Variable Segments of the Heavy Chain that are
                        Members of the VH6 Gene Family"

( x i ) SEQUENCE DESCRIPTION: SEQ ID NO:16:

CAGGTACAGC TGCTCGAGTC AGGTCCA                                                                       27

( 2 ) INFORMATION FOR SEQ ID NO:17:

( i ) SEQUENCE CHARACTERISTICS:
                ( A ) LENGTH: 58 base pairs
                ( B ) TYPE: nucleic acid
                ( C ) STRANDEDNESS: single
                ( D ) TOPOLOGY: linear ( i i ) MOLECULE TYPE: cDNA ( i i i ) HYPOTHETICAL: NO ( i v ) ANTI-SENSE: NO ( i x ) FEATURE:
                ( A ) NAME/KEY: misc_RNA (B) LOCATION: 1..58
        (D) OTHER INFORMATION: /label=CK1d
            / note= ""CK1d"refers to the cDNA Primer for Kappa
            Light Chain Constant Segments"

(xi) SEQUENCE DESCRIPTION: SEQ ID NO:17:

GCGCCGTCTA GAATTAACAC TCTCCCCTGT TGAAGCTCTT TGTGACGGGC GAACTCAG    58

(2) INFORMATION FOR SEQ ID NO:18:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_RNA
        (B) LOCATION: 1..24
        (D) OTHER INFORMATION: /label=VK1a
            / note= ""VK1a"refers to the cDNA Primer for
            Variable Segments of the Kappa Light Chain that
            are Members of the VK1 Gene Family"

(xi) SEQUENCE DESCRIPTION: SEQ ID NO:18:

GACATCGAGC TCACCCAGTC TCCA    24

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_RNA
        (B) LOCATION: 1..24
        (D) OTHER INFORMATION: /label=VK2a
            / note= ""VK2a"refers to the cDNA Primer for
            Variable Segments of the Kappa Light Chain that
            are Members of the VK2 Gene Family"

(xi) SEQUENCE DESCRIPTION: SEQ ID NO:19:

GATATTGAGC TCACTCAGTC TCCA    24

(2) INFORMATION FOR SEQ ID NO:20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: misc_RNA ( B ) LOCATION: 1..24
                    ( D ) OTHER INFORMATION: /label=VK3a
                            / note= ""VK3a"refers to the cDNA Primer for
                            Variable Segments of the Kappa Light Chain that
                            are Members of the VK3 Gene Family"

( x i ) SEQUENCE DESCRIPTION: SEQ ID NO:20:

GAAATTGAGC TCACGCAGTC TCCA                                                          2 4

( 2 ) INFORMATION FOR SEQ ID NO:21:

( i ) SEQUENCE CHARACTERISTICS:
                    ( A ) LENGTH: 22 base pairs
                    ( B ) TYPE: nucleic acid
                    ( C ) STRANDEDNESS: single
                    ( D ) TOPOLOGY: linear ( i i ) MOLECULE TYPE: cDNA ( i x ) FEATURE:
                    ( A ) NAME/KEY: misc_RNA
                    ( B ) LOCATION: 1..22
                    ( D ) OTHER INFORMATION: /note= "5'Heavy Chain Sequencing
                            Primer"

( x i ) SEQUENCE DESCRIPTION: SEQ ID NO:21:

GGCCGCAAAT TCTATTTCAA GG                                                            2 2

( 2 ) INFORMATION FOR SEQ ID NO:22:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: cDNA ( i x ) FEATURE:
                    ( A ) NAME/KEY: misc_RNA
                    ( B ) LOCATION: 1..18
                    ( D ) OTHER INFORMATION: /note= "3'Heavy Chain Sequencing
                            Primer"

( x i ) SEQUENCE DESCRIPTION: SEQ ID NO:22:

CGCTGTGCCC CCAGAGGT                                                                 1 8

( 2 ) INFORMATION FOR SEQ ID NO:23:

( i ) SEQUENCE CHARACTERISTICS:
                    ( A ) LENGTH: 18 base pairs
                    ( B ) TYPE: nucleic acid
                    ( C ) STRANDEDNESS: single
                    ( D ) TOPOLOGY: linear ( i i ) MOLECULE TYPE: cDNA ( i x ) FEATURE:
                    ( A ) NAME/KEY: misc_RNA
                    ( B ) LOCATION: 1..18
                    ( D ) OTHER INFORMATION: /note= "5'Light Chain Sequencing
                            Primer"

( x i ) SEQUENCE DESCRIPTION: SEQ ID NO:23:

CTAAACTAGC TAGTCGCC                                                                 1 8

( 2 ) INFORMATION FOR SEQ ID NO:24:

( i ) SEQUENCE CHARACTERISTICS:
                    ( A ) LENGTH: 21 base pairs
                    ( B ) TYPE: nucleic acid
                    ( C ) STRANDEDNESS: single

```
( D ) TOPOLOGY: linear ( i i ) MOLECULE TYPE: cDNA ( i x ) FEATURE:
        ( A ) NAME/KEY: misc_RNA
        ( B ) LOCATION: 1..21
        ( D ) OTHER INFORMATION: /note= "3'Light Chain Sequencing
              Primer"

( x i ) SEQUENCE DESCRIPTION: SEQ ID NO:24:

ATAGAAGTTG TTCAGCAGGC A                                                    21
```

METHODS FOR SELECTIVELY DETECTING PERINUCLEAR ANTI-NEUTROPHIL CYTOPLASMIC ANTIBODY OF ULCERATIVE COLITIS, PRIMARY SCLEROSING CHOLANGITIS, OR TYPE 1 AUTOIMMUNE HEPATITIS

This is a continuation-in-part of prior pending U.S. patent application Ser. No. 08/320,163 filed on Oct. 7, 1994, which is a continuation of the now abandoned U.S. patent application Ser. No. 08/028,784 filed on Mar. 10, 1993.

FIELD OF THE INVENTION

This invention relates to methods and kits for detecting and measuring the presence or absence of perinuclear anti-neutrophil cytoplasmic antibodies of ulcerative colitis, primary sclerosing cholangitis, or type 1 autoimmune hepatitis. More specifically, the methods and kits of the present invention employ DNAase treatment of neutrophils in assays such as ELISA and immunofluorescence to elicit the loss of a positive control value when the antibody is present.

BACKGROUND OF THE INVENTION

Inflammatory Bowel Disease (IBD) is the collective term used to describe two gastrointestinal disorders, ulcerative colitis ("UC") and Crohn's disease ("CD"). IBD occurs world-wide and is reported to afflict as many as two million people. Onset has been documented at all ages; however, IBD predominately affects young adults.

The three most common presenting symptoms of IBD are diarrhea, abdominal pain, and fever. The diarrhea may range from mild to severe and is often accompanied by urgency and frequency. In UC, the diarrhea is usually bloody and may contain mucus and purulent matter as well. Anemia and weight loss are additional common signs of IBD.

A battery of laboratory, radiological, and endoscopic evaluations are combined to derive a diagnosis and to assess the extent and severity of the disease. Nevertheless, differentiating UC from CD, as well as other types of inflammatory conditions of the intestines, such as irritable bowel syndrome, infectious diarrhea, rectal bleeding, radiation colitis, and the like, is difficult. Indeed, depending on the period of follow-up time, in many patients the colitis must be regarded as indeterminate or cannot be definitively diagnosed because of the overlapping features of UC and CD, particularly with CD of the colon.

The selective identification of UC as opposed to CD or other inflammatory conditions of the intestines carries important prognostic and therapeutic implications. For example, when colectomy is indicated, the type of IBD involved determines which surgical options are appropriate. Surgery (total colectomy) does represent a cure in UC, though a dramatic one. In CD, surgery is never curative. Continent procedures such as the ileorectal pull-through (mucosal proctectomy) or the Kock pouch may be desirable in UC, but are contraindicated in CD.

The availability of a diagnostic marker that would readily distinguish UC from CD of the colon and other colitides would represent a major clinical advance. A convenient and reliable blood test which might parallel disease activity or even predict an impending flare of activity would provide a tremendous advantage in the therapeutic management of IBD and aid in the design of more specific treatment modalities.

Although the cause(s) of UC and CD not known, there is general agreement that the immune system is responsible for mediating the tissue damage in these diseases. A wide range of immunologic abnormalities have been reported in these disorders, but none has yet been sufficiently reliable to be of diagnostic value.

A variety of autoantibodies has been observed in UC patients. Most notable among these antibodies have been lymphocytotoxic antibodies and colonic epithelial antibodies. Although these may have genetic and pathophysiologic implications, they have not been useful diagnostically either because of low frequency of occurrence or lack of specificity.

Two other inflammatory diseases which are also suspected of having autoimmune eitologies are primary sclerosing cholangitis ("PSC") and type 1 autoimmune hepatitis ("Type 1 AIH"). Like UC and CD, these liver diseases share common outward symptoms necessitating the use of invasive technologies, such as liver biopsy and/or ERCP to identify distinguishing liver abnormalities associated with AIH and PSC.

PSC is characterized by obliterative inflammatory fibrosis of the extrahepatic bile ducts with or without involvement of the intrahepatic ducts. The disease generally progresses in an unrelenting, albeit unpredictable, fashion to cirrhosis, portal hypertension, and death from liver failure. PSC can occur alone or in association with UC and less commonly with a variety of other diseases. Symptoms commonly include jaundice, puritis and nonspecific upper abdominal pain. Medical treatment of PSC has included corticosteroids, antibiotics, immunosuppressants, and cholecystogues alone or in combination. In general, results with all have been disappointing.

AIH is a disorder of unknown etiology in which progressive destruction of the hepatic parenchyma occurs, often progressing to cirrhosis, and in the more severe cases, it carriers a high mortality rate if untreated. Although this disease is predominant in women, it also affects men. Easy fatigability is the most common symptom at presentation, and up to 77% of patients also describe features of jaundice, mild upper abdominal discomfort, pruritus, anorexia, polymyalgias, diarrhea, and delayed menarche or amenorrhea are frequent complaints. Cosmetic change, including facial rounding, hirsutism, and acne. The histologic hallmark of AIH is periportal, or piecemeal, necrosis. The condition is considered incurable with a poor prognosis; spontaneous or sustained remission if considered rare. Combined treatment prednisone and azathioprine has been reported to significantly improve life expectancy and normalize clinical, biochemical and immunochemical abnormalities. Type 1 AIH is the most common form of autoimmune hepatitis in the United States, and it is associated with smooth-muscle antibody or antinuclear antibody seropositivity, hypergammaglobulinemia, concurrent immunologic disorders, HLA positivity for A1, B8, DR3, or DR4, and responsive to corticosteroid therapy.

p-ANCA recently has been demonstrated to be associated with both Type 1 AIH and PSC. It is reported that p-ANCA has been found in up to 70% of PSC patient sera while up to 92% of the sera of patients with well defined Type 1 AIH were found to express high titer pANCA. However, this discovery has been of limited clinical applicability in the diagnosis of these hepatobiliary inflammatory diseases due to an inability to differentiate between the p-ANCA associated with each disease.

Accordingly, there has existed a need for a convenient and reliable method to distinguish UC from CD of the colon, and PSC from Type 1 AIH for diagnostic, prognostic and therapeutic purposes.

SUMMARY OF THE INVENTION

The present invention provides methods of detecting and measuring the presence or absence of perinuclear anti-neurtrophil cytoplasmic antibodies ("p-ANCA") of ulcerative colitis ("UC"), primary sclerosing cholangitis ("PSC") or type 1 autoimmune hepatitis ("Type 1 AIH") in a sample. More specifically, the presence of p-ANCA of UC, PSC or Type 1 AIH is detected by assaying for the loss of a positive value (i.e., loss of a detectable marker as compared to a control) upon treatment of neutrophils with DNAase. The present invention demonstrates that the p-ANCA associated with Type 1 AIH is different from that associated with PSC and that each of those p-ANCA are different than the p-ANCA related to UC. These differences can be relied upon to screen for each of the p-ANCA, the p-ANCA associated disease, and to differentiate between the three.

In one embodiment of the present invention, methods of measuring the presence or absence of perinuclear anti-neurtrophil cytoplasmic antibodies (p-ANCA) associated with ulcerative colitis, primary sclerosing cholangitis, or type 1 autoimmune hepatitis in a sample, comprising contacting the sample and a detectable secondary antibody with fixed, DNAase-treated neutrophils under conditions suitable to form a complex of neutrophil, p-ANCA and detectable secondary antibody, separating unbound secondary antibody from the complex, and assaying for the pattern of p-ANCA immunoreactivity by detecting the presence, absence or pattern of complexed secondary antibody, compared to a control. DNAase treatment of neutrophils result in substantially complete digestion of cellular DNA without significant loss of nuclear or cellular morphology. The control is the result of repeating the inventive method on a sample from the same source, except that the neutrophils are not subjected to DNAase treatment.

The present invention also provides kits containing reagents useful for identifying the presence or absence of p-ANCA of UC, PSC or AIH in a sample. The kits include, among other reagents, fixed neutrophil and a detectable secondary antibody.

DETAILED DESCRIPTION OF THE INVENTION

Figure 1A:
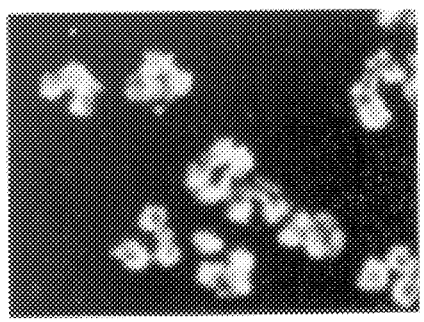
FIG. 1 illustrates the differentiation between p-ANCA of PSC and p-ANCA of Type I AIH. (A) p-ANCA staining pattern generated by Type I AIR serum with methanol-fixed neutrophils before DNAase digestion. (B) p-ANCA staining pattern generated by PSC serum with methanol-fixed neutrophil before DNAase digestion. (C) Granular cytoplasmic staining pattern generated with Type I AIH serum with DNAase-treated neutrophils. (D) Homogeneous (mushy) cytoplasmic staining pattern generated by PSC serum with DNAase-treated neutrophils.

The present invention provides methods and kits for detecting the presence of perinuclear anti-neutrophil cytoplasmic autoantibody (p-ANCA) for ulcerative colitis (UC), primary sclerosing cholangitis (PSC) or type 1 autoimmune hepatitis (Type 1 AIH) in a sample. Inventive methods involve assaying for the loss of a positive value (as compared to a control) upon treatment of neutrophils with DNAase. The inventive methods also involve the detecion of a particular staining pattern which can be correlated to the presence of a particular disease associated p-ANCA.

As the name indicates, antibodies to cytoplasmic components of the neutrophil are found in the serum of patients with certain chronic inflammatory conditions. By immunofluorescent microscopy, ANCA activity has been divided into two broad categories: cytoplasmic neutrophil staining (refered to herein as "c-ANCA staining pattern" or "cytoplasmic staining pattern") and cytoplasmic staining with perinuclear highlighting (refered to herein as "p-ANCA staining pattern" or "perinuclear staining pattern"). These distinct staining patterns are obtained with alcohol-fixed cytocentrifuged neutrophils. It has been reported that the p-ANCA staining pattern is an artifact of alcohol fixation which results when cytoplasmic granules re-locate to the periphery of the nucleus during the fixation process. However, the present invention provides evidence that the perinuclear staining pattern of p-ANCA associated with UC is not artifactual, but rather is the result of specific binding with a DNA associated antigen. Nevertheless, whether alcohol induced or actual, these staining patterns have served to distinguish between types of ANCA arising from unique antigens and having different disease associations.

The methods of the present invention exploit the unique staining patterns of UC, PSC and Type 1 AIH, as compared to one another, CD and other inflammatory conditions of the intestines, to provide a convenient and reliable method of identifying UC, PSC or Type 1 AIH, eliminating the uncertainty formerly associated with diagnosing and treating IBD and these liver diseases One aspect of the present invention relates to methods of measuring the presence or absence of p-ANCA of UC or PSC in a sample, comprising: (a) contacting the sample and a detectable secondary antibody with immobilized neutrophils under conditions suitable to form a complex of neutrophil, p-ANCA and detectable secondary antibody, wherein said immobilized neutrophil is subjected to DNAase under conditions sufficient to cause substantially complete digestion of cellular DNA without significant loss of nuclear or cellular morphology prior to said contacting step, and wherein said secondary antibody has specificity for p-ANCA or the class determining portion of p-ANCA; (b) separating unbound secondary antibody from the complex; (c) assaying for the presence or absence of p-ANCA containing complex by measuring the presence or absence of bound secondary antibody, compared to a control, wherein said control is the result of repeating the steps of the present method on a sample from the same source, except that the neutrophil of step (a) is not subjected to DNAase treatment.

In a related embodiment of the invention, the same method in an indirect immunofluorescence assay format can be used to detect the presence or absence of p-ANCA associated with Type I AIH, as well as the presence or absence of p-ANCA UC or PSC. Accordingly, there is provided a method of measuring the presence or absence of p-ANCA associated with UC, PSC, or Type 1 AIH in a sample, said method comprising: (a) contacting the sample and a detectable secondary antibody with fixed neutrophils under conditions suitable to form an immune complex of neutrophil, p-ANCA and detectable secondary antibody, wherein said fixed neutrophils are subjected to DNAase under conditions sufficient to cause substantially complete digestion of cellular DNA without significant loss of nuclear or cellular morphology prior to said contacting step, and wherein said secondary antibody has specificity for the class determining portion of p-ANCA; (b) separating unbound secondary antibody from the immune complex; (c) assaying for the pattern of p-ANCA immunoreactivity by detecting the presence, absence or pattern of complexed secondary antibody, compared to a control, wherein said control is the result of repeating the present method on a sample from the same source, except that the neutrophils are not subjected to DNAase.

As used herein the terms "complex" or "immune complex" refer to the product of specific bining between an antigenic determinant-containing molecule, such as an antigen, and a molecule containing an antibody combining site such as, for example, an antibody molecule. The term "immunoreactivity," as used herein, refers to the ability or attribute of a molecule containing an antibody combining site, for example an antibody molecule and the like, to specifically bind an antigenic determinant-containing molecule such as, for example, an antigen and the like.

In the methods of the present invention, neutrophils are subjected to DNAase under conditions sufficient to cause substantially complete digestion of cellular DNA. By the term "complete digestion of cellular DNA" it is meant such digestion of the cellular DNA that the cellular DNA has substantially lost its ability to bind proteins and other cellular materials normally associated with the cellular DNA of the neutrophil. Without being bound by any particular theory, it is presently believed that at least part of the antigens of p-ANCA of UC and PSC are proteins that are either intimately associated with nuclear DNA or with some aspects of nuclear structure.

Conditions sufficient to cause substantially complete digestion of cellular DNA will vary in accordance with the purity and concentration of the DNAase used and include, for example, incubating the immobilized neutrophil in a concentration of DNAase of about 2 to 10 units of DNAase per milliliter of a suitable buffer for a time in the range of about 15 minutes to one hour at a temperature in the range of about 22° C. to 40° C.

The assays of the present invention may be forward, reverse or simultaneous as described in U.S. Pat. No. 4,376,110, issued Mar. 8, 1983 to David et al., incorporated herein by reference in its entirety. In the forward assay, each reagent is sequentially contacted with immobilized neutrophils. If desired, separation of bound from unbound reagent can be accomplished before the addition of the next reagent. In a reverse assay, all reagents are pre-mixed prior to contacting immobilized neutrophil. A modified method of a reverse assay is described in U.S. Pat. No. 4,778,751 issued Oct. 18, 1988 to El Shami et al., incorporated herein by reference in its entirety. In a simultaneous assay, all reagents are separately but contemporaneously contacted with the immobilized neutrophil. The steps of the presently preferred inventive assay are discussed in further detail below.

As used herein, the term "reagent" refers to any component useful to perform the assays of the present invention, for example, the sample, the primary antibody, the detectible secondary antibody, washing buffers, solutions, and the like.

A sample can be obtained from any biological fluid, for example, whole blood, plasma, or other bodily fluids or tissues having p-ANCA, preferably serum.

The separation steps for the various assay formats described herein, including removing unbound secondary antibody from the complex, can be performed by methods known in the art. When appropriate, a simple washing with a suitable buffer followed by filtration or aspiration is sufficient. If the neutrophils are immobilized on a particulate support, as in the case of microparticles for example, it may be desirable to centrifuge the particulate material, followed by removal of wash liquid. If the neutrophil(s) immobilized on membranes or filters, applying a vacuum or liquid absorbing member to the opposite side of the membrane or filter allows one to draw the wash liquid through the membrane or filter.

The methods of the present invention are normally carried out at room temperature and 37° C. Because the methods involve the use of proteins, temperatures which would substantially modify the tertiary and quaternary structures of the proteins should be avoided. Accordingly, temperatures suitable for performing the methods of the present invention generally range from about 22° C. to about 38° C.

In a preferred embodiment of the present invention, neutrophils are immobilized on a solid substrate. The solid substrate can be any support useful in immunometric assays. The substrate can be made from natural or synthetic material which is insoluble in water and can be rigid or non-rigid. However, the substrate should not significantly affect the desired activity of the neutrophils. Preferred substrates include glass slides, test wells made from polyethylene, polystyrene, nylon, nitrocellulose, glass and the like. Also useful are test tubes, filter paper, filtering devices such as glass membranes, beads, and particulate materials such as agarose, cross-linked dextran and other polysaccharides, and the like.

In accordance with the methods and kits of the present invention, immobilization of neutrophils can be accomplished by any method known in the art. Preferably, a method of immobilization is used that renders the neutrophils permeable to DNAase and the reagents used in the methods and kits of the present invention. For example, neutrophils can be immobilized by fixing them directly to the surface of a test well or glass slide with suitable fixative, such as, for example, methanol, ethanol, formalin, or the like. Of course, one of skill in the art will appreciate that such fixative should not substantially alter nuclear or cellular morphology of the neutrophils.

Neutrophils and secondary antibody appropriate for use in the practice of the present invention will depend upon the origin of the sample assayed. As used herein, the terms "patient," "subject," or "individual" when referring to the origin of the sample to be assayed, means any animal capable of producing p-ANCA of UC, PSC or Type 1 AIH, including for example, humans, non-human primates, rabbits, rats, mice, and the like. Preferably, neutrophils and secondary antibody employed will have specific reactivity for the species from which the sample to be tested is obtained. For example, to assay for p-ANCA of UC, PSC, or Type I AIH in a sample obtained from a human subject, the neutrophils and the secondary antibody are preferably specific for humans. If multiple antibodies are employed, each antibody is preferably species-specific for its antigen.

Neutrophils useful in the present invention can be obtained from a variety of sources, e.g., the blood of a human, non-human primates, rabbits, rats, mice, and the like, by methods known to those of skill in the art.

The term "secondary antibody" as used herein, refers to any antibody or combination of antibodies or fragments thereof, at least one of which can bind p-ANCA of UC, PSC, or Type I AIH. For example, a secondary antibody can be an anti-p-ANCA antibody, specific for any epitope of p-ANCA, but preferably not one that would be competitive with neutrophil binding or cause steric hinderance of neutrophil/p-ANCA binding. Alternatively, a secondary antibody can be an anti-IgG preferably having specificity for the class determining portion of p-ANCA.

Secondary antibodies useful in the practice of the present invention can be obtained by techniques well known in the art. Such antibodies can be polyclonal or preferably monoclonal. Polyclonal antibodies can be obtained, for example, by the methods in Ghose et al., *Methods of Enzymology*, Vol. 93, 326–327 (1983). For example, IgG or Fc fragments of IgG can be used as the immunogen to stimulate the production of IgG reactive polyclonal antibodies in the antisera of animals such as rabbits, goats, sheep, rodents, and the like.

Monoclonal antibodies useful in the practice of the present invention can be obtained from a number of commercially available sources. Alternatively, the antibodies can be obtained, for example, by the process described by Milstein and Kohler in *Nature*, 256:495–97 (1975) or as modified by Gerhard, *Monoclonal Antibodies*, 370–371 (Plenum Press, 1980). If a mouse anti-human IgG antibody is desired, a mouse is first injected with an immunogen containing, for example, human IgG or Fc fragments of human IgG. The mouse is subsequently sacrificed and cells taken from its spleen are fused with myeloma cells by methods well known in the art. The resulting hybridomas are screened to isolate clones that secrete a single antibody specie reactive with human IgG.

Preferably, the hybridomas are screened to identify those producing antibodies that are highly specific for the IgG of interest. The monoclonal antibody selected will have an affinity compatible with the desired sensitivity and range for detecting p-ANCA of UC or PSC. The use of such monoclonal antibodies provides a means of obtaining greater sensitivity in the assays of the present invention compared with the use of polyclonal antibodies.

Alternatively, monoclonal antibodies having a high affinity for p-ANCA of UC or PSC can be obtained by the creation of a phage combinatorial library for p-ANCA of UC or PSC and then screening for specificity by a similar process described in Barbas, C. F. et al, *Proceedings of the Nat'l Academy of Science*, 88:7978–82 (1991), incorporated herein by reference. The Examples below exemplify methods for making a phage combinatorialy library of an immunoglobulin gene repertoire for UC, as well as methods of screening the library for p-ANCA associated with UC. The nucleic acid and deduced amino acid sequence of the immunoglobulin heavy and light Fab chains of the two clones (5-3 and 5-4) of p-ANCA associated with UC are provided in SEQ ID NO:1 through 8. Anti-idiotypic antibodies to these and other clones of p-ANCA associated with UC can be raised by methods well known in the art. For example, polyclonal and monoclonal antibodies can be produced as described, for example, in Harlow and Lane, *Antibodies: A Laboratory Manual* (Cold Spring Harbor Laboratory 1988), which is incorporated herein by reference.

The phrase "monoclonal antibody" in its various grammatical forms refers to a population of antibody molecules that contain only one species of idiotype capable of immunoreacting with a particular epitope on an antigen or idiotope on an antibody. A monoclonal antibody typically displays a single binding affinity for an epitope or idiotope with which it immunoreacts; however, a monoclonal antibody may be a molecule having a plurality of idiotopes, each immunospecific for a different epitope or idiotope, e.g., a bispecific monoclonal antibody.

Monoclonal antibodies are typically composed of antibodies produced by clones of a single cell called a hybridoma that secretes (produces) but one kind of antibody molecule. In accordance with the present invention hybridomas capable of producing antibody material having specific immunoreactivity with p-ANCA associated with UC, but which does not prevent immunoreactivity of p-ANCA with neutrophil is provided. Such a hybridoma cell is formed by fusing an antibody-producing cell and a myeloma or other self-perpetuating cell line. The preparation of such hybridomas was first described by Kohler and Milstein, *Nature*, 256:495–497 (1975), which description is incorporated by reference. Polypeptide-induced hybridoma technology is also described by Niman et al., *Proc. Natl. Sci., U.S.A.*, 80:4949–4953 (1983), which description is also incorporated herein by reference.

To obtain an antibody-producing cell for fusion with an immortalized cell, a mammal is inoculated with an immunogen. The word "immunogen" in its various grammatical forms is used herein to describe a composition containing a p-ANCA associated with UC as an active ingredient used for the preparation of the antibodies against p-ANCA associated with UC.

The amount of p-ANCA associated with UC used to inoculate the mammal should be sufficient to induce an immune response to the immunizing polypeptide. This amount depends, among other things, on the species of animal inoculated, the body weight of the animal and the chosen inoculation regimen as is well known in the art. Inocula typically contain about 10 micrograms of immunogen per inoculation for mice and may contain up to about 500 milligrams of immunogen per inoculation for larger mammals.

The spleen cells of the mammal immunized with p-ANCA associated with UC are then harvested and can be fused with myeloma cells using polyethylene glycol (PEG) 1500. Fused hybrids are selected by their sensitivity to HAT. Hybridomas producing an anti-p-ANCA idiotypic monoclonal antibody can be identified by screening hybridoma supernatants for the presence of antibody molecules that immunoreact with p-ANCA associated with UC. Such screening methods include for example, radioimmunoassay (RIA) or enzyme linked immunosorbent assay (ELISA).

Media useful for the preparation of these compositions are well known in the art and commercially available and include synthetic culture media, inbred mice and the like. An exemplary synthetic medium is Dulbecco's minimal essential medium (DMEM; Dulbecco et al., Virol., 8:396 (1959)) supplemented with 4.5 gm/l glucose, 20 mm glutamine, and 20% fetal calf serum. An exemplary inbred mouse strain is the Balb/c.

Another alternative for increasing the sensitivity of the assay of the present invention is to use a multiple antibody system for the secondary antibody, rather than using a single antibody with enhanced specificity. Thus, the methods of the present invention may be performed using a combination of antibodies as the secondary antibody, wherein at least one secondary antibody of the combination has specificity for p-ANCA or the class determining portion of p-ANCA and at least one secondary antibody of the combination is detectable. For example, UC and PSC may be distinguished from Crohn's disease in a sample of human blood by contacting two aliquots of blood serum from a patient with immobilized untreated or DNAase treated human neutrophil, followed by contacting the resulting antibody-antigen complex with mouse anti-human IgG. The resulting complex is then contacted with goat anti-mouse IgG having a detectable label and washed to remove unbound antibody. The resulting complex is assayed for the presence or absence of a detectable complex, compared to the control (i.e., non-DNAase treated neutrophil). The absence of the labeled goat anti-mouse IgG complexed with DNAase-treated neutrophils indicates that the patient has UC or PSC.

The term "detectible secondary antibody" refers to secondary antibody, as defined above, that can bind p-ANCA of UC or PSC and can be detected or measured by a variety of analytical methods. This term includes antibodies, or fragments thereof, that are directly detectible without attachment of signal generating labels, or those that can be labeled with a signal generating system to permit detection or measurement, such as, for example, any secondary antibody capable of being labeled with a radioisotope, enzyme, chromogenic or fluorogenic substance, a chemiluminescent marker, or the like. Alternatively, a secondary antibody can be made detectible by using biotin-avidin linkage to associate a label with the secondary antibody. In any of the above methods, the reactivity of the secondary antibody with the p-ANCA should not be significantly altered by the presence of the label. When a multi-antibody system is used as the secondary antibody, at least one of the antibodies, combination of antibodies or fragments thereof is capable of binding p-ANCA of UC or PSC, and at least one can readily be detected or measured by suitable analytical methods.

Detectible markers can be bound to the secondary antibody by procedures known to those skilled in the art such as, for example, the chloramine-T procedure for radioactive markers, enzymatically by the lactoperoxidase procedure, by the Bolton-Hunter techniques or any other technique known in the art. These techniques plus others are well known to those of skill in the art and are described, for example, in Methods in Enzymology, Volume 70, Part A (Van Vunakis and Langone, editors 1980).

Thus, the secondary antibody can be bound to enzymes such as, for example, horseradish peroxidase, luciferase, malate dehydrogenase, glucose-6-phosphate dehydrogenase, alkaline phosphatase, and the like. The presently preferred enzyme is alkaline phosphatase. Dual channeled catalytic systems may also be used in the methods of the present invention, including, for example, alkaline phosphatase and glucose oxidase using glucose-6-phosphate as the initial substrate. Suitable catalytic systems are described in U.S. Pat. No. 4,366,241, issued Dec. 28, 1982 to Tom et al., U.S. Pat. No. 4,740,468, issued Apr. 26, 1988 to Weng et al., U.S. Pat. No. 4,843,000, issued Jun. 27, 1989 to Litman et al., and U.S. Pat. No. 4,849,338, issued Jul. 18, 1989 to Litman et al., all of which are herein incorporated by reference in their entirety.

The procedures for attaching enzymes to various substances are well known in the art. For example, techniques for coupling enzymes to antibodies are described in J. H. Kennedy et al., Clin. Chim. Acta, 70:1 (1976). Reagents useful for such coupling include, for example, glutaraldehyde, p-toluene diisocyanate, various carbodiimide reagents, p-benzoquinone m-periodate, N,N'-orthophenylenedimaleimide, and the like.

Alternatively, secondary antibody linked to a detectable enzyme useful for the methods and kits of the present invention may be obtained from a number of commercially available sources, for example, goat F(ab')2 anti-human IgG-alkaline phosphatase may be purchased from Jackson Immuno-Research, located in West Grove, Pa. Suitable substrates for the above-described enzymatic systems include simple chromogens and fluorogens such as, for example, beta-D-glucose, homovanillic acid, o-dianisidine, bromocresol purple powder, 4-methyl-umbelliferone, luminol, para-dimethylaminolophine, paramethoxylophine, para-nitrophenyl phosphate, and the like. The presently preferred enzyme substrate is para-nitrophenylphosphate.

Secondary antibody may also be rendered detectable by chemically linking it to a fluorogenic compound. Suitable fluorogenic compounds are those that emit light in ultraviolet or visible wavelength subsequent to excitation by light or other energy source. The fluorogens can be employed alone or with a suitable quencher molecule. Presently preferred fluorogens are fluorescein, fluorescein isothiocyanate, tetramethyl-rhodamine isothiocynate, 7-amino-4-methylcoumarin-3-acetic acid and phycoerythrin. The methods of conjugating and using these and other suitable fluorogens have been reported and are described, for example, in Methods in Enzymology, Volume 74, Part C, 32105 (Van Vunakis and Langone, Editors 1991).

Alternatively, secondary antibody linked to fluorogen useful for the practice of the present invention may be obtained from a number of commercially available sources, for example, goat F(ab')2 anti-human IgG-FITC available from Tago Immunologicals, Burlingame, Calif.

Depending on the nature of the label or catalytic signal producing system used, a signal can be detected by irradiating the complexed test sample with light and observing the level of fluorescence; by contacting the complexed sample with a substrate which can be catalytically converted by the label to produce a dye, fluorescence or chemiluminescence, in which the formation of dye can be observed visually or in a spectrophotometer; fluorescence can be observed visually or in a fluorometer; or, in the case of chemiluminescence or a radioactive label, by employing a radiation counter such as a gamma counter or gamma emitting markers such as iodine-125. For enzyme-catalyzed systems, when the presently preferred combination of alkaline phosphatase is used as the enzyme and para-nitrophenyl phosphate as the substrate, a color change may be detected visually for a qualitative positive reaction. For a quantitative analysis of the same or similar system, EMAX Microplate Reader (available from Molecular Devices, Menlo Park, Calif.) at 405 nm may be used in accordance with the manufacturer's instructions.

In accordance with the present invention, the presence or absence of p-ANCA of UC or PSC in the sample being tested is determined by contacting a sample with immobilized, DNAase treated neutrophils and secondary antibody, and assaying for the presence or absence of p-ANCA containing complex. The presence or absence of p-ANCA containing complex is determined by monitoring for the presence or absence of bound secondary antibody, compared to a control. P-ANCA is considered present in the test sample if there exists a loss of positive value (bound secondary antibody) in the test sample as compared to the control. The control is the result of repeating the same steps of the inventive method on a sample from the same source, when the immobilized neutrophil has not been subjected to DNAase.

For example, in an IIF assay format of the present methods the presence of p-ANCA of UC in a sample, and thus UC itself, is indicated when there is a loss of a perinuclear staining pattern, i.e., detectable complex associated with perinuclear staining pattern, as compared to said control. More preferably, the presence of p-ANCA of UC is further indicated by the absence of both a perinuclear staining pattern and a cytoplasmic staining pattern in the sample. Similarly, using the same IIF assay format the presence of p-ANCA of PSC in a sample, and thus PSC itself, is indicated when a homogeneous cytoplasmic staining pattern is detected in the sample and a perinuclear staining pattern is detected in the control, i.e., "conversion of detectable complex associated with perinuclear staining pattern to homogenous cytoplasmic staining pattern, as compared to said control." Likewise, using the same IIF assay format, the presence of p-ANCA of Type 1 AIH in a sample, and thus Type 1 AIH itself, is indicated when a granular cytoplasmic staining pattern is detected in the sample and a perinuclear staining pattern is detected in the control, i.e., "conversion of detectable complex associated with perinuclear staining pattern to granular cytoplasmic staining pattern, as compared to said control." Finally, CD is indicated if the absence of a perinuclear staining pattern in the control is detected, i.e., "absence of a detectable complex associated with perinuclear staining pattern in said control."

In this manner, the methods of the present invention can be used to distinguish between p-ANCA of UC, p-ANCA of PSC and p-ANCA of Type 1 AIH, as well as to screen for any one of these p-ANCA, and thereby, preferably in combination with traditional diagnostic techniques, screen for any one of the diseases and distinguish them from CD.

For example, sera from 94 patients diagnosed with UC which were seropositive for p-ANCA, sera from ten patients diagnosed with PSC which were seropositive for p-ANCA, and sera from 22 patients diagnosed with Type I AIH which were seropositive for very high titre p-ANCA (mean ELISA value for neutrophil binding 139±8) were analyzed for DNAase sensitivity in accordance with the methods of the present invention using a IIF assay format. As summarized in Table 1, loss of antigenic recognition after DNAase digestion of neutrophils demonstrated by the absence of any staining pattern is a dominant (66/94, 70%) characteristic of p-ANCA associated with UC.

TABLE 1

Reactions of p-ANCA expressing sera with DNase treated neutrophils

| | | No Treatment | Post DNAase Treatment | |
| --- | --- | --- | --- | --- |
| | | Neutrophil Staining Pattern | | |
| Disease | n | perinuclear | None | cANCA |
| UC | 94 | 94/94 (100%) | 66/94 (70%) | 28/94 (30%) |
| Type 1 AIH | 22 | 22/22 (100%) | 3/22 (14%) | 19/22 (86%) |
| PSC (w/o UC) | 10 | 10/10 (100%) | 3/10 (30%) | 7/10 (70%) |

On the other hand, the majority of p-ANCA associated with PSC and p-ANCA associated with Type 1 AIH p-ANCA recognize cytoplasmic components after DNAase treatment of neutrophils (7/10, 70% and 19/22, 86% respectively). When the patient sera is grouped based on whether the patient had UC or not (Table 2, UC/non-UC), it becomes clear that loss of perinuclear staining pattern after DNAase treatment of neutrophil is unique to p-ANCA of UC providing a reliable basis on which to screen for UC and differentiate p-ANCAs.

TABLE 2

Comparison of p-ANCA of UC and group of p-ANCA associated with diseases other than UC.

| | | No Treatment | Post DNAase Treatment | |
| --- | --- | --- | --- | --- |
| | | Neutrophil Staining Pattern | | |
| Disease | n | perinuclear | None | cANCA |
| UC | 94 | 94/94 (100%) | 66/94 (70%) | 28/94 (30%) |
| non-UC | 32 | 32/32 (100%) | 6/32 (19%) | 26/32 (81%) |

The differentiation between p-ANCA of PSC and p-ANCA of Type 1 AIH is based upon the specific cytoplasmic staining pattern produced with DNAase treated neutrophil. As exemplified in by the drawing, the perinuclear staining pattern of p-ANCA positive PSC sera (FIG. 1B) in the majority of sera tested became cytoplasmic but with a characteristically mushy, or stated more scientifically, homogenous staining pattern (FIG. 1D). By comparison, the perinuclear staining pattern generated by Type 1 AIH serum with methanol-fixed neutrophils (FIG. 1A) in the majority of sera tested also became cytoplasmic, but with a characteristically granular staining pattern (FIG. 1C).

Accordingly, another embodiment of the invention provides methods of detecting the presence or absence of p-ANCA associated with Type I AIH in a sample, comprising: (a) contacting fixed neutrophils with a sample and a detectable secondary antibody under conditions suitable to form an immune complex of neutrophil, p-ANCA and detectable secondary antibody, wherein cellular DNA of the fixed neutrophils has been digested by DNAase without significant loss of nuclear or cellular morphology, and wherein the detectable secondary antibody is detectable by fluorescence and is specific for the class determining portion of p-ANCA; (b) separating unbound secondary antibody from the immune complex; and (c) detecting the immunofluorescent staining pattern of the complex as compared to a control, wherein the control is the result of repeating the present method using fixed neutrophils wherein the cellular DNA of the fixed Neutrophils has not been digested by DNAase, and wherein the presence of a granular cytoplasmic staining pattern in the sample, and a perinuclear staining pattern in the control, indicates the presence of p-ANCA associated with type 1 autoimmune hepatitis in the sample. The skilled artisan will appreciate that the control as described above, is generated using neutrophil which has been fixed in the same manner as the neutrophil used to test the sample, but that the neutrophils used to generate the control have not been subjected to treatment i.e., digestion, with DNAase.

In accordance with another embodiment of the present invention, there is provided methods of detecting the presence or absence of p-ANCA associated with PSC in a sample, comprising: (a) contacting fixed neutrophils with a sample and a detectable secondary antibody under conditions suitable to form an immune complex of neutrophil, p-ANCA and detectable secondary antibody, wherein cellular DNA of the fixed neutrophils has been digested by DNAase without significant loss of nuclear or cellular morphology, and wherein the detectable secondary antibody is detectable by fluorescence and is specific for the class determining portion of p-ANCA; (b) separating unbound secondary antibody from the immune complex; and (c) detecting the immunofluorescent staining pattern of the complex as compared to a control, wherein the control is the result of repeating the present method using fixed neutrophils wherein the cellular DNA of the fixed neutrophils has not been digested by DNAase, and wherein the presence of a homogenous cytoplasmic staining pattern in the sample, and a perinuclear staining pattern in the control, indicates the presence of p-ANCA associated with primary sclerosing cholangitis in the sample.

In yet another embodiment of the present invention there is provided, methods of differentiating p-ANCA of PSC from p-ANCA of Type I AIH, and thus differentiating between the presence of the diseases, comprising: (a) contacting fixed neutrophils with a sample and a detectable secondary antibody under conditions suitable to form an immune complex of neutrophil, p-ANCA and detectable secondary antibody, wherein cellular DNA of the fixed neutrophils has been digested by DNAase without significant loss of nuclear or cellular morphology, and wherein the detectable secondary antibody is detectable by fluorescence and is specific for the class determining portion of p-ANCA; (b) separating unbound secondary antibody from the immune complex; and (c) detecting the immunofluorescent staining pattern of the complex as compared to a control, wherein the control is the result of repeating the present method using fixed neutrophils wherein the cellular DNA of the fixed neutrophils has not been digested by DNAase, and wherein the presence of a homogeneous cytoplasmic staining pattern in the sample and a perinuclear staining pattern in the control indicates PSC, and wherein the presence of a granular cytoplasmic staining pattern in the sample and a perinuclear staining pattern in the control indicates Type I AIH.

In yet another embodiment of the present invention there is provided, methods of differentiating p-ANCA of UC from p-ANCA of Type I AIH, and thus differentiating between the presence of the diseases, comprising: (a) contacting fixed neutrophils with a sample and a detectable secondary antibody under conditions suitable to form an immune complex of neutrophil, p-ANCA and detectable secondary antibody, wherein cellular DNA of the fixed neutrophils has been digested by DNAase without significant loss of nuclear or cellular morphology, and wherein the detectable secondary antibody is detectable by fluorescence and is specific for the class determining portion of p-ANCA; (b) separating unbound secondary antibody from the immune complex; and (c) detecting the immunofluorescent staining pattern of the complex as compared to a control, wherein the control is the result of repeating the present method using fixed neutrophils wherein the cellular DNA of the fixed neutrophils has not been digested by DNAase, and wherein the absence of a perinuclear staining pattern in the sample, and preferably the absence of a cytoplasmic staining pattern in the sample as well, and a perinuclear staining pattern in the control sample indicates UC, and wherein the presence of a granular cytoplasmic staining pattern in the sample and a perinuclear staining pattern in the control indicates Type I AIH.

In still another embodiment of the present invention there is provided methods of differentiating between p-ANCA of UC, p-ANCA of PSC, and p-ANCA of Type 1 AIH, and thus differentiating between the presence of the diseases, said method comprising: (a) contacting fixed neutrophils with a sample and a detectable secondary antibody under conditions suitable to form an immune complex of neutrophil, p-ANCA and detectable secondary antibody, wherein cellular DNA of the fixed neutrophils has been digested by DNAase without significant loss of nuclear or cellular morphology, and wherein the detectable secondary antibody is detectable by fluorescence and is specific for the class determining portion of p-ANCA; (b) separating unbound secondary antibody from the immune complex; and (c) detecting the immunofluorescent staining pattern of the complex as compared to a control, wherein the control is the result of repeating the present method using fixed neutrophils wherein the cellular DNA of the fixed neutrophils has not been digested by DNAase, and wherein absence of a perinuclear staining pattern in the sample, and preferably the absence of a cytoplasmic staining pattern in the sample as well, and the presence of a perinuclear staining pattern in the control indicates UC; wherein the conversion of detectable complex associated with perinuclear staining pattern to homogenous cytoplasmic staining pattern, as compared to said control, indicates PSC; wherein conversion of detectable complex associated with perinuclear staining pattern to granular cytoplasmic staining pattern, as compared to said control, indicates Type I AIH; and wherein absence of a detectable complex associated with perinuclear staining pattern in said control indicates CD.

In another aspect of the present invention, kits for measuring the presence of the p-ANCA of UC, PSC, or Type 1 AIH in a sample are provided. A kit of the present invention can contain immobilized, DNAase-treated, alcohol fixed neutrophils and a detectable secondary antibody. Alternatively, a kit may contain immobilized neutrophils, DNAase and a detectable secondary antibody. Optionally, depending on the secondary antibody or label used, the kits may contain a signal generating substance to provide or enhance the detection of the p-ANCA of UC, PSC or Type 1 AIH. In addition, other components such as ancillary reagents may be included, for example, stabilizers, buffers, fixatives, such as methanol or ethanol, and the like. The reagents can be provided as dry powders, usually lyophilized, including excipients, which on dissolution will provide a reagent solution having the appropriate concentrations for performing the methods of the present invention.

A preferred embodiment of the inventive kit includes DNAase and human neutrophils immobilized on a solid substrate, preferably a microtiter plate or beads for detecting or quantitating fluorescence by a cell sorter. To detect the presence of p-ANCA of UC, PSC or Type 1 AIH, the kit preferably includes mouse anti-human IgG, and goat anti-mouse IgG labeled with an enzyme or a fluorogenic substance.

In yet another aspect of the present invention there is provided an isolated antigen of UC. The antigen naturally occurs in neutrophils and is characterized by its insolubility in Triton X-100™ which can be obtained from Fisher, Pittsburgh, Pa., catalogue number BP-151.

In yet another aspect of the present invention there is provided an isolated antigen of PSC. The antigen naturally occurs in neutrophils and is characterized by its insolubility in Triton X-100™.

The invention will now be described in greater detail by reference to the following non-limiting examples.

EXAMPLE I

SEPARATION OF HUMAN PERIPHERAL BLOOD LYMPHOCYTES BY FICOLL-HYPAQUE GRADIENT CENTRIFUGATION

1. Add 31.8 g Ficoll 400 (Pharmacia, Sweden) to 400 ml deionized $H_2O$ in a 500 ml bottle. Shake vigorously until dissolved. Add 100 ml of 500 sodium diatrizoate hypaque (UCLA Pharmacy, Los Angeles, Calif.) and mix.

2. Check specific gravity using a hydrometer. It should be 1.077–1.080.

3. Filter-sterilize Ficoll-hypaque solution through a 0.22 or 0.45 um bottle top filter. The Ficoll-hypaque solution may be stored at 4° C., protected from light.

4. Pour 15 ml Ficoll-hypaque solution into a 50 ml conical centrifuge tube. Carefully overlayer 30 ml heparinized blood.

5. Centrifuge at 1000×g (2000 RPM) for 20 min.

6. Remove interface using a serologic pipet or pasteur pipet and place into 50 ml conical centrifuge tube.

7. Dilute interface layer with at least an equal volume of Hanks' Balanced Salt Solution (HBSS) (Irvine Scientific, Santa Ana, Calif.).

8. Centrifuge at 400×g (1200 RPM) for 5 min.

9. Decant supernatant, resuspend pellet, and add 50 ml HBSS.

10. Repeat twice steps 8 and 9.

11. Resuspend cells in RPMI 1640 (Irvine Scientific, Santa Ana, Calif.) +5 fetal calf serum (GIBCO, Gathersberg, Md.).

EXAMPLE II

ISOLATION OF NEUTROPHIL

1. Using a pipet, carefully remove serum and remaining Ficoll-Hypaque from red blood cell pellet resulting from procedure described in Example I.

2. Add 10 ml 60 dextran to 15 milliliters of pellet.

3. Top off with 1× HBSS to 50 ml. Re-suspend pellet.

4. Allow red blood cells to settle, approximately 45 minutes to one hour.

5. Separate supernatant, discard pellet. Top supernatant off with 1× HBSS to 50 ml and centrifuge for 5 minutes at 1800 rpm.

6. Decant supernatant and tap pellet. Hypotonically lyse remaining red blood cells by adding 9 ml deionized water, swirl, and then add 1 ml 10× HBSS and immediately dilute with 1× HBSS to 50 ml.

7. Centrifuge for 5 minutes at 1000 rpm. Discard supernatant and re-suspend pellet in 15 ml 1× HBSS.

EXAMPLE III

IMMOBILIZATION OF Neutrophils ON GLASS SLIDES

1. Count cells in suspension of step 7 of Example II using a microscope and hemacytometer and re-suspend cells in sufficient volume of 1× HBSS to achieve $2.5 \times 10^6$ cells per ml.

2. Use Cytospin 3™ (Shandon, Inc. Pittsburgh, Pa.) at 500 rpm for 5 minutes to apply 0.01 ml of the re-suspended cells to each slide.

3. Fix cells to slide by incubating slides for 10 minutes in sufficient volume of 100% methanol to cover sample. Allow to air dry. The slides may be stored at −200° C.

EXAMPLE IV

DNAase TREATMENT OF Neutrophils IMMOBILIZED ON GLASS SLIDE

Prepare a DNAase solution by combining 3 units of Promega RQ1™ DNAase per ml buffer containing 40 mM of TRIS-HCl (pH 7.9), 10 mM of sodium chloride, 6 mM magnesium chloride and 10 mM calcium chloride. Promega RQ1™ DNAase can be obtained from Promega, of Madison, Wis.

Rinse slides prepared in accordance with Example III with about 100 ml phosphate buffered saline (pH 7.0–7.4) for 5 minutes. Incubate immobilized neutrophils in 0.05 ml of DNAase solution per slide for about 30 minutes at 37° C. Wash the slides three times with about 100–250 ml phosphate buffered saline at room temperature.

EXAMPLE V

IMMUNOFLUORESCENCE ASSAY

1. Add 0.05 ml of a 1:20 dilution of human sera in phosphate buffered saline to slides treated with DNAase in accordance with Example IV and to untreated slides of Example III. Add 0.05 ml phosphate buffered saline to clean slides as blanks. Incubate for 0.5 to 1.0 hours at room temperature in sufficient humidity to minimize volume loss.

2. Rinse off sera by dipping into a container having 100–250 ml phosphate buffered saline. Soak slide in phosphate buffered saline for 5 minutes. Blot lightly.

3. Add 0.05 ml goat $F(ab')_2$ anti-human $IgG(\mu)$-FITC, at a 1:1000 antibody:phosphate buffered saline dilution, to each slide. Incubate for 30 minutes at room temperature, in sufficient humidity to minimize volume loss. (Goat $F(ab')_2$ anti-human $IgG(\mu)$-FITC is available from Tago Immunologicals, Burlingame, Calif. and from Jackson Immunoresearch Laboratories, Baltimore, Md.).

4. Rinse off antibody with 100–250 ml phosphate buffered saline. Soak slides for 5 minutes in 100–250 ml phosphate buffered saline, then allow to air dry.

5. Read fluorescence pattern on fluorescence microscope at 40×.

If desired, any DNA can be stained with propidium iodide stain by rinsing slides well with phosphate buffered saline at room temperature and stain for 10 seconds at room temperature. Wash slide three times with 100–250 ml phosphate buffered saline at room temperature and mount cover slip.

EXAMPLE VI

DNAase SENSITIVITY OF UC p-ANCA SPECIFIC ANTIGEN USING IMMUNOFLUORESCENCE ASSAY DNAase obtained from Promega was used at a working concentration of 3 units/ml. DNAase concentration was optimized by titrating the amount of DNAase added (from 1 to 10 units/ml) and examining the extent of DNA digestion by propidium iodide staining and/or reaction with anti-DNA antisera. Digestion of cytocentrifuged, methanol-fixed neutrophils was carried out at 37° C. for 30 minutes with DNAase solubilized in 40 mM Tris-HCl (pH 7.9) buffer containing 10 mM NaCl, 6 mM $MgCl_2$ and 10 mM $CaCl_2$. Virtually all cellular DNA was lost, as indicated by the lack of propidium iodide staining. Also lost was the reaction of an anti-histone positive serum. DNAase reaction carried out as described herein, however, does not significantly alter nuclear or cellular morphology.

Neutrophils treated with trypsin at various concentrations no longer reacted with UC p-ANCA positive sera nor with anti-histone positive serum, indicating that at least part of the p-ANCA reactive antigen is a protein. Similarly, pepsin digestion of neutrophils abolished PSC p-ANCA positive serum reaction, also indicating a proteinaceous character of that antigenic species. Panels of UC p-ANCA positive and c-ANCA positive patient sera were examined for DNAase sensitivity using cytocentrifuged, methanol-fixed slides as described above. Two other types of reactions were noted. Some p-ANCA positive sera lost the perinuclear aspect of the reaction and became cytoplasmic after DNAase treatment, while c-ANCA positive sera generally remained cytoplasmic. Additionally, some sera that were found to have both a perinuclear and cytoplasmic ANCA staining reaction always lost the perinuclear aspect of the reaction after DNAase treatment of neutrophils. These DNAase-induced staining patterns proved to be highly reproducible from experiment to experiment.

This data indicates at least three ANCA reactions are possible in response to DNAase treatment of immobilized neutrophils; 1) a p-ANCA reaction that is abolished, 2) a p-ANCA reaction that becomes cytoplasmic and 3) a c-ANCA reaction that persists. In all of these cases, the DNAase digestion was complete as evidenced by a lack of propidium iodide staining as well as lack of reaction by anti-DNA antibody.

Figure 2A:
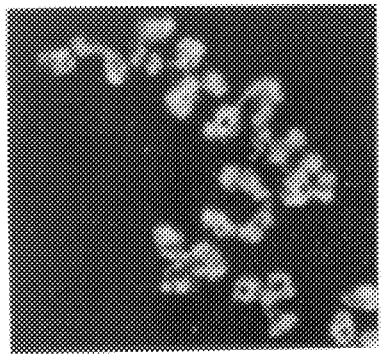
FIG. 2 illustrates the staining patterns generated with UC patient serum previously characterized as containing p-ANCA. (A) p-ANCA staining pattern generated with p-ANCA positive UC serum on untreated neutrophil. (B) Staining pattern generated with p-ANCA positive UC serum on untreated neutrophil. (C) Abolition of p-ANCA staining pattern with p-ANCA positive UC serum after DNAase treatment of neutrophil- (D) Cytoplasmic (c-ANCA) homogeneous (or mushy) staining pattern with p-ANCA positive UC serum after DNAase treatment of neutrophil.
Figure 2B:
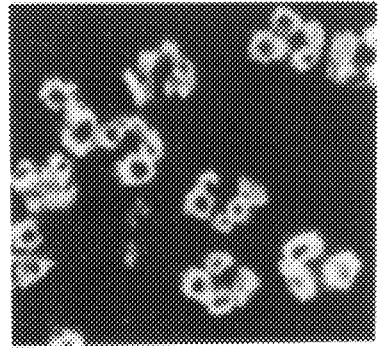
Figure 2C:
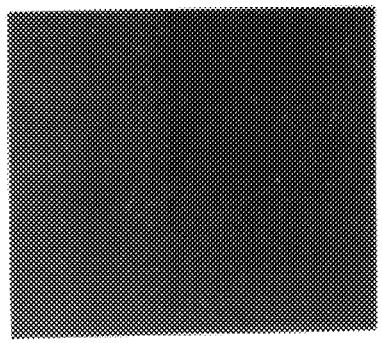
Figure 2D:
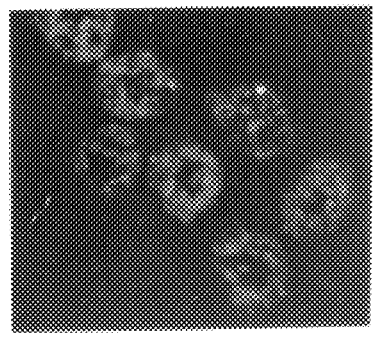

To determine whether DNAase treatment of neutrophils would abolish the antigenic recognition of all p-ANCA associated with UC, a panel (n=94) of UC patient sera, previously characterized as containing p-ANCA was examined for neutrophil binding after DNAase treatment using the IIF assay format. In 70% of the UC sera tested, DNAase treatment again resulted in the abolition of the immunogenic reaction that results in a p-ANCA staining pattern (FIG. 2A and C). The remaining p-ANCA positive UC sera were found to give a cytoplasmic (c-ANCA) homogeneous (or mushy) staining pattern after DNAase treatment of neutrophils (FIG. 2B and D). Thus, p-ANCA associated with UC yielded two possible reactions after DNAase treatment of neutrophils; 1) a p-ANCA reaction that is abolished and 2) a p-ANCA reaction that converts to a c-ANCA staining pattern. These changes in neutrophil staining patterns obtained after DNAase treatment of cells were a consistent feature of the sera tested and the same results were obtained in multiple experiments.

Finally, it was also examined whether prior reaction of neutrophils with p-ANCA positive serum would effect the DNAase sensitivity of antigen. The perinuclear reaction is maintained even after DNAase digestion when neutrophils are first treated with the p-ANCA positive serum. This result indicates a protective effect of antibody binding against either physical loss of antigen or loss of epitope recognition.

EXAMPLE VII

COMPARATIVE CHARACTERIZATION OF UC p-ANCA IMMUNOREACTIVE

Figure 3A:
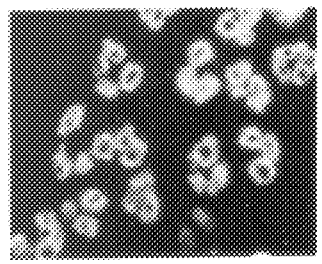
FIG. 3 illustrates the indirect immunofluorescent staining patterns generated with p-ANCA positive UC patient serum, anti-DNA serum and propidium iodide on methanol-fixed neutrophil (top row) and DNAase-treated, methanol-fixed neutrophil (bottom row). (A) Staining pattern generated with p-ANCA positive UC serum on methanol-fixed neutrophil, (B) Staining pattern generated with anti-DNA serum on methanol-fixed neutrophil. (C) Propidium iodide staining of methanol-fixed neutrophil. (D) Staining pattern generated with p-ANCA positive UC serum on DNAase-treated, methanol-fixed neutrophil. (E) Staining pattern generated with anti-DNA serum on DNAase-treated, methanol-fixed neutrophil. (F) Propidium iodide staining of DNAase-treated, methanol-fixed neutrophil.
Figure 3B:
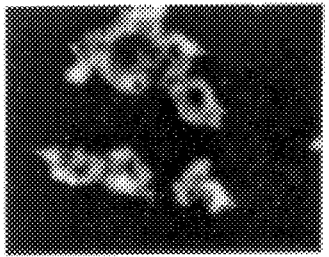
Figure 3C:
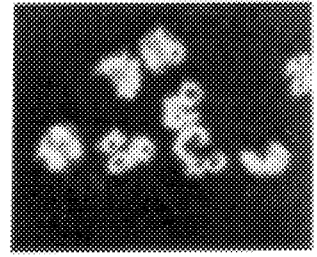
Figure 3D:
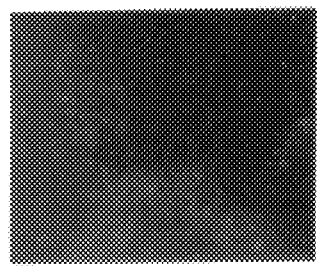
Figure 3E:
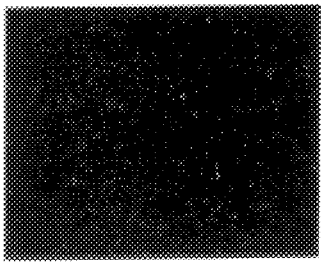
Figure 3F:
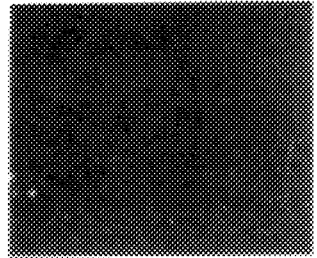
Figure 4A:
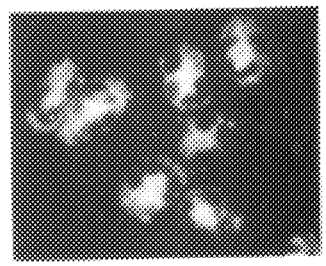
FIG. 4 illustrates the indirect immunofluorescent staining patterns generated with WG serum, serum that expresses anti-elastase antibodies and serum that expresses antibodies antibodies to PR3 on methanol-fixed neutrophil (top row) and DNAase-treated, methanol-fixed neutrophil (bottom row). (A) Staining pattern generated with WG serum on methanol-fixed neutrophil. (B) Staining pattern generated with anti-elastase serum on methanol-fixed neutrophil. (C) Staining pattern generated with anti-PR3 serum on methanol-fixed neutrophil. (D) Staining pattern generated with WG serum on DNAase-treated, methanol-fixed neutrophil. (E) Staining pattern generated with anti-elastase serum on DNAase-treated, methanol-fixed neutrophil. (F) Staining pattern generated with anti-PR3 serum on DNAase-treated, methanol-fixed neutrophil.
Figure 4B:
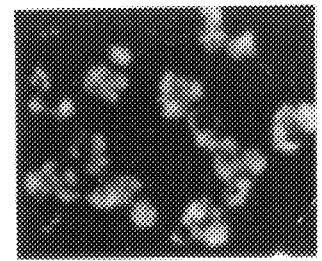
Figure 4C:
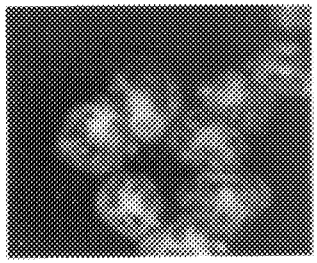
Figure 4D:
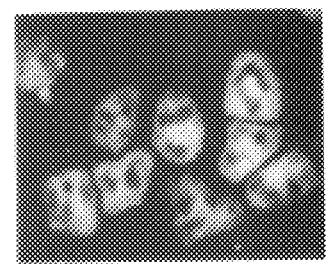
Figure 4E:
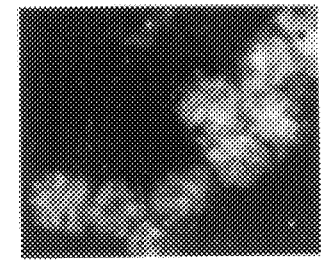
Figure 4F:
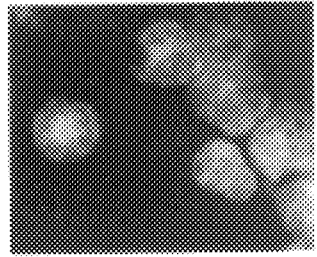

To examine whether DNA integrity was necessary for UC p-ANCA binding to neutrophils, methanol-fixed neutrophils were treated with DNAase, contacted with p-ANCA positive serum from a patient diagnosed with UC, and UC specific p-ANCA binding examined by IIF. For comparative purposes the binding of a non-UC sera were also tested. Serum that expresses anti-DNA antibodies (Rheumatology Diagnostics Laboratories Inc., Los Angeles, Calif.), a serum that expressed WG ANCA, a serum that expresses anti-elastase antibodies, and that serum expresses antibodies to PR3 (the latter three all obtained from J. Charles Jennette University of North Carolina, Chapel Hill) were also contacted with DNAase treated, methanol-fixed neutrophils and binding examined by IIF. Additionally, the effectiveness of the DNAase digestion and subsequent loss of DNA was routinely monitored by staining neutrophils with the DNA binding dye, propidium iodide. FIG. 3 and 4 provide for comparison the IIF staining patterns generated with these serum with methonal-fixed neutrophil (top row) and DNAase-treated, methanol-fixed neutrophil (bottom row). As seen in FIG. 3A and D, the p-ANCA staining pattern generated by p-ANCA positive UC serum (FIG. 3A) is completely lost when neutrophil are pre-treated with DNAase (FIG. 3D) indicating that UC p-ANCA binding is abolished. A similar loss of antigen recognition after DNAase treatment was obtained, as expected, with the anti-DNA serum. FIG. 3B depicts the IIF staining pattern of anti-DNA serum on untreated neutrophils. This staining pattern is clearly lost when neutrophils are pre-treated with DNAase. (FIG. 3E) That DNAase treatment of neutrophils was effective in eliminating cellular DNA is seen in the lack of propidium iodide staining after such treatment (FIG. 3F) as compared to the propidium iodide staining pattern in the absence of DNAase treatment. (FIG. 3C) Neutrophil binding by WG serum was unchanged (FIG. 4A and D) by DNAase treatment of the cells while the anti-elastase p-ANCA staining pattern (FIG. 4B) was converted to a granular cytoplasmic pattern (FIG. 4E) by DNAase treatment. Finally, the staining pattern generated by anti-PR3 (FIG. 4C and F) was also unaffected by the DNAase digestion of neutrophils.

EXAMPLE VIII

COMPARATIVE DNAase SENSITIVITY OF PSC p-ANCA SPECIFIC ANTIGEN AND TYPE 1 AIH SPECIFIC ANTIGEN USING IMMUNOFLUORESCENCE ASSAY A panel of p-ANCA-containing sera from PSC and Type 1 AIH patients was examined and compared to the UC sera panel.

All the sera were previously characterized with respect to ANCA staining pattern by IIF and ANCA binding level as determined by ELISA. Representative ANCA staining patterns before and after DNAase digestion of neutrophils are given in FIG. 1.

Figure 1B:
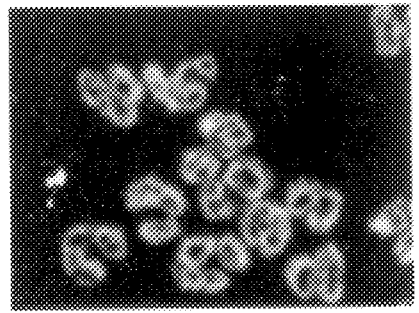
Figure 1C:
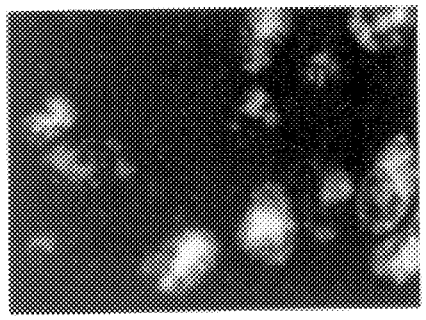
Figure 1D:

The p-ANCA staining pattern generated by Type 1 AIH serum with methanol-fixed neutrophils is depicted in FIG. 1A. This p-ANCA positive Type 1 AIH serum was characteristically found to yield a granular cytoplasmic staining pattern with DNAase digested neutrophils. (FIG. 1C) The p-ANCA staining pattern generated by serum of patients diagnosed with PSC is depicted in FIG. 1B. PSC sera yielded a predominantly homogenous (mushy) cytoplasmic staining pattern with DNAase treated neutrophils (FIG. 1D).

EXAMPLE IX

IMMOBILIZATION OF Neutrophils ON MICROTITER PLATE

1. Count cells in suspension of step 7 of Example II using a microscope and hemacytometer and re-suspend cells in sufficient volume of 1× HBSS to achieve $2.5 \times 10^6$ cells per ml. Add 0.1 ml per well to a 96-well microtiter Immulon 1™ or Immulon™ plate (available from Dynatech Laboratories of Chantilly, Va.) and let settle for 30–60 minutes.

2. Pull supernatant with 8 channel manifold connected to a vacuum and let plate air dry (approximately 2 hours) or turn upside down on the grate of a laminar flow hood to dry (approximately 10 minutes).

3. Fix cells to well by incubating cells for 10 minutes in 0.1 ml of 100% methanol per well. Discard methanol and let plate air dry. Store at −20° C.

EXAMPLE X

DNAase TREATMENT OF NEUTROPHILS IMMOBILIZED ON MICROTITER PLATE

A DNAase solution is prepared by combining 3 units of Promega RQ1™ DNAase per ml buffer containing 40 mM of Tris-HCl (pH 7.9), 10 mM sodium chloride, 6 mM magnesium chloride and 10 mM calcium chloride.

Rinse plates prepared in accordance with Example VII once with 25 ml phosphate buffered saline. Incubate immobilized neutrophils in 0.1 ml of DNAase solution per well for about 30 minutes at 37° C. Wash the wells three times with a total of about 100 ml phosphate buffered saline. Block the wells by adding 0.15 ml of 0.25% bovine serum albumin in phosphate buffered saline (pH 7.4) and allowing to stand at room temperature for about one hour. Discard blocking fluid.

EXAMPLE XI

DNAase-TREATED, FIXED NEUTROPHIL ELISA

1. Add 0.1 ml human sera diluted as desired with phosphate buffered saline containing 0.25% bovine serum albumin to each well of the microtiter plates prepared in accordance with Example VIII and Example VII (i.e., with and without the DNAase treatment). Add 0.01 ml phosphate buffered serum containing 0.25% bovine serum albumin to blank wells. Let stand at room temperature for one hour, in sufficient humidity to minimize volume loss.

2. Aspirate serum. Wash three times with a total of about 100 ml phosphate buffered saline containing 0.02% sodium azide ($NaN_3$) and 0.056 Tween.

3. Add to each well 0.1 ml of a 1:1000 dilution of alkaline phosphatase-coupled goat anti-human IgG antibody in phosphate buffered saline containing 0.25% bovine serum albumin. Goat $F(ab')_2$ anti-human IgG(Fc)-alkaline phosphatase may be obtained from Jackson Immuno-Research Laboratories in West Grove, Pa. Incubate for one hour at room temperature in sufficient humidity to minimize volume loss.

4. Wash three times with a total of 100 ml phosphate buffered saline containing 0.02% sodium azide ($NaN_3$) and 0.05% Tween. Wash three more times with TRIS-NaCl solution containing 0.05M Tris, 0.15M NaCl, and 0.02% sodium azide, pH 7.5.

5. Combine 0.75 g disodium p-nitrophenol phosphate (United States Biochemicals catalogue #19587 or AMRESCO catalogue #P0364) with a Tris buffer containing 75 mM Tris-HCl, 1.5 mM $MgCl_2$, 0.02% sodium azide, pH 8.6 to form a substrate containing solution. Add 0.01 ml substrate containing solution to each well. Incubate at room temperature for 60 to 90 minutes in sufficient humidity to minimize volume loss, until blank wells reach 0.8 in absorbance.

6. Read plate at 405 nm in an EMAX Microplate Reader (Molecular Devices, Menlo Park, Calif.)

EXAMPLE XII

CHANGE IN ANCA BINDING TO DNAase TREATED NEUTROPHILS RELATIVE TO CONTROL UNTREATED CELLS USING DNAase-TREATED, FIXED NEUTROPHIL ELISA In a panel of p-ANCA positive UC sera, the subset found to lose greater than 50% of ANCA binding by ELISA corresponds to those that lost most or all of the p-ANCA staining by immunofluorescent staining. On the other hand, sera showing less than about 50% reduction in ANCA binding by ELISA were found to display a p-ANCA pattern that converted to cytoplasmic staining after DNAase digestion of neutrophils. In this latter group was also found a few sera with a mixture of perinuclear/cytoplasmic staining pattern that retained only the cytoplasmic pattern post DNAase treatment. The one serum displaying a cytoplasmic ANCA staining pattern was found to have increased ANCA binding post DNAase treatment. The majority (4 out of 6) of p-ANCA positive PSC sera lost less than 50% of the ANCA binding after DNAase treatment of neutrophils; in contrast only 5 out of 14 UC p-ANCA positive sera showed such a loss. By immunofluorescent staining these PSC sera were found to display a p-ANCA staining pattern that became cytoplasmic after DNAase treatment.

Thus, the DNAase-treated, fixed neutrophil ELISA may be used to distinguish UC and PSC from CD, as well as other types of inflammatory conditions of the intestines. The unique perinuclear/cytoplasmic staining patterns associated with immunofluorescent-type assays confirms the reliability of ELISA assay and may allow further distinctions between UC and PSC.

EXAMPLE XIII

ANCA IN PEDIATRIC ULCERATIVE COLITIS

In the pediatric population, distinguishing between UC, Crohn's disease (CD) and allergic colitis in children with rectal bleeding (RB) is particularly difficult. Since the occurrence of ANCA in adult patients with UC has been well established, studies were undertaken to determine the relationship between the occurrence of ANCA and pediatric UC. To determine whether the presence of ANCA, as measured by DNAase-treated fixed-neutrophil ELISA is sensitive and specific for pediatric UC, serum from children with UC (mean age=13), CD (mean age=14), RB (mean age=3) and other gastrointestinal inflammatory disorders (mean age=8) were tested in a blinded fashion. All ELISA positive samples were examined using immunofluorescence assay described above to determine ANCA staining patterns. ANCA was expressed as a percentage of UC positive sera binding and defined as positive when the value exceeded 2 standard deviations above the mean for normal control sera ($\geq$12%). The results are presented in Table 3.

TABLE 3

ANCA IN PEDIATRIC ULCERATIVE COLITIS

| | # | #ANCA+ | MEAN<br>% Positive Cont. | | MEAN<br>Reciprocal Titer | |
|---|---|---|---|---|---|---|
| | Patients | (%) | Total | ANCA+ | Total | ANCA+ |
| UC | 29 | 21 (72) | 44 | 57 | 527 | 705 |
| CD | 41 | 7 (17) | 8 | 16 | 61 | 114 |
| RB | 13 | 3 (23) | 8 | 17 | 87 | 208 |
| Non-IBD | 94 | 7 (7) | 6 | 21 | 63 | 229 |

UC = ulcerative colitis
CD = Crohn's disease
RB = rectal bleeding

Seventy-two percent of children with UC were ANCA positive compared to 17% with CD, 23% with RB and 7% with other gastrointestinal inflammatory disorders (Table 1). The mean percent of positive control at 1:100 dilution was also significantly higher in UC (p<0.00 vs CD and non-IBD, p<0.01 vs RB). In addition, mean titers of ANCA positive samples were significantly higher, making ELISA titer very specific for UC. The presence of a perinuclear immunofluorescence pattern correlated with titer. It is therefore seen that ANCA is sensitive (72%) and specific (89%) for UC versus other inflammatory disorders.

EXAMPLE XIV

ANTIGEN REACTIVE WITH p-ANCA OF UC AND PSC IS TRITON X-100™ INSOLUBLE

1. Count cells in suspension of step 7 of Example II using a microscope and hemacytometer and re-suspend cells in sufficient volume of phosphate buffered saline containing 1.0% Triton X-100™ to acheive $2.5 \times 10^6$ cells per ml phosphate buffered saline containing 0.5% Triton X-100™. Allow to incubate on ice for about 10 minutes.

2. Cytocentrifuge onto glass slide as described in Example III, step 2.

3. Fix cytocentrifuged Triton X-100™ extract in accordance with the procedure set forth in Example III, step 3.

4. Add 0.05 ml of a 1:20 dilution of UC p-ANCA positive serum or PSC p-ANCA positive serum in phosphate buffered saline to slides. Add 0.05 ml phosphate buffered saline to clean slides as blanks. Incubate for 30 minutes to one hour at room temperature in sufficient humidity to minimize volume loss.

5. Process slides in accordance with the immunofluorescence assay of Example V, steps 2–5.

After Triton X-100™, neutrophil morphology was clearly lost with no evidence of a clear nuclear structure upon reaction with anti-DNA serum. However, cellular DNA was not lost during Triton X-100™ treatment. Both UC p-ANCA positive sera and PSC p-ANCA positive sera showed strong reactivity with fixed Triton X-100™ neutrophil extract. Based upon Triton X-100™ insolubility, an enriched fraction of UC and PSC p-ANCA antigens can be prepared to isolate the antigens.

EXAMPLE XV

LIBRARY CONSTRUCTION $V_H$- and $V_L$-encoding DNA homolog libraries of the heavy and light chain gene repertoire of lamina propria lymphocytes (LPL) cells from humans diagnosed with UC and seropositive for p-ANCA in a fixed neutrophil ELISA were randomly combined, expressed and the resulting antibody material screened for ability to bind neutrophil using a phage display technique. The antibody material having immunoreactivity with neutrophil were then screened for p-ANCA staining pattern and for loss of the p-ANCA staining pattern using DNAase-treated neutrophil as means of identifying p-ANCA associated with UC.

These variable heavy and light chain libraries were constructed by PCR cloning of variable heavy and light chains from these LPL. The homologs from these libraries were randomly paired in the dicistronic phagemid expression vector pComb 3 as described herein, resulting in a variable heavy chain fusion protein containing the $V_H$ polypeptide and a fragment of the filamentous phage coat protein III. E. coli were subsequently transformed with these vectors containing the DNA-encoding heterodimeric antibody material. Expression of the vectors was induced and the cells transformed with helper phage. Phage that were extruded from the transformed E. coli encapsulated the vector DNA encoding the nucleotide sequence and displayed the encoded heavy and light chains as Fab antibody material anchored to the phage coat via the gene III anchor protein. This phagemid expression system thus links both the process of recognition and replication in a single phage particle.

In a process called panning as described by Parmley et al., Gene, 74: 305–318 (1988), the phage expressing heterodimeric antibody material having anti-neutrophil immunoreactivity are enriched and isolated. The heterodimeric antibody material is then assayed for further the presence of p-ANCA associated with UC by alcohol-fixed indirect immunofluorescence ("the IIF assay") and for loss of a positive p-ANCA staining pattern in the IIF assay using DNAase-treated alcohol-fixed neutrophil.

$V_H$ and $V_L$ Library Generation

Nucleotide sequences encoding immunoglobulin protein CDRs are highly variable. However, there are several regions of conserved sequences that flank the V domains of the light and heavy chains that contain substantially conserved nucleotide sequences, i.e., sequences that will hybridize to the same primer sequence.

Polynucleotide synthesis ("amplification") primers that hybridize to these conserved sequences and incorporate restriction sites into the DNA homolog produced, restriction sites that are suitable for operatively ligating the DNA homolog to a vector, were constructed. More specifically, the primers are designed so that the resulting DNA homologs produced can be inserted into an expression vector in reading frame with the upstream translatable DNA sequence at the region of the vector containing the directional ligation means. Amplification with the primers described herein is performed on cDNA templates produced from total RNA isolated from LPL of a human diagnosed with UC and seropositive for p-ANCA.

$V_H$ Primers

For amplification of the $V_H$ domains, primers are designed to introduce cohesive termini compatible with directional ligation into the unique Xho I and Spe I sites of the Hc2 expression cassette of the pComb 3 phagemid expression vector. In all cases, the 5' primers listed in SEQ ID NOs:10 through 16 are chosen to be complimentary to the first strand cDNA in the conserved N-terminus region (anti-sense strand).

Additional $V_H$ amplification primers, including the unique 3' primer, are designed to be complimentary to a portion of the first constant region domain of gamma 1 heavy chain mRNA (SEQ ID NO:9). These primers will produce DNA homologs containing polynucleotides coding for amino acids from the $V_H$ domain and the first constant region domain of immunoglobulin heavy chains of the IgG isotype. These DNA homologs can therefore be used to produce Fab fragments rather than $F_V$.

Additional unique 3' primers designed to be hybridized to similar regions of another class of immunoglobulin heavy chain such as IgM, IgE and IgA are contemplated. Other 3' primers that hybridize to a specific region of a specific class of $CH_1$ constant region and are adapted for transferring the $V_H$ domains amplified using this primer to an expression vector capable of expressing those $V_H$ domains with a different class of heavy or light chain constant regions are also contemplated.

Amplification is performed in seven separate reactions, each containing one of the 5' primers shown in SEQ ID NOS:10 through 16, and a 3' primer shown in SEQ ID NO:9. The 5' primers incorporate a Xho I site and the 3' primers incorporate a Spe I restriction site for the insertion of the $V_H$-encoding DNA homolog into the Hc2 expression cassette of the pComb 3 phagemid expression vector. See, Barbas, C. F. et al., *Proceedings of the National Academy of Science*, 88: 7978–7982 (1991), incorporated herein by reference.

$V_L$ Primers

For amplification of the $V_L$ domains, amplification primers are constructed that hybridize to the conserved sequences of immunoglobulin light chains and that incorporate restriction sites that allow cloning the $V_L$-encoding DNA homologs into the Lc2 expression cassette of the pComb 3 phagemid expression vector cut with Sac I and Xba I. The 5' primers (SEQ ID NOS:18 through 20) are designed to be complimentary to the first strand cDNA in the conserved N-terminus region. These primers also introduce a Sac I restriction endonuclease site to allow the $V_L$-encoding DNA homologs to be cloned into the pComb 3 phagemid Lc2 expression cassette. The 3' $V_L$ amplification primer (SEQ ID NO:17) is designed to hybridize to the constant region of kappa cDNA and to introduce the Xba I restriction endonuclease site required to insert $V_L$-encoding DNA homologs into the pComb 3 phagemid Lc2 expression cassette. These primers allow DNA homologs to be produced that encode immunoglobulin light chains of the kappa isotype. These primers make it possible to produce a Fab fragment rather than a Fv.

Amplification of the immunoglobulin light chain gene repertoire is performed in three separate reactions, each containing one of the 5' primers (SEQ ID NOS:18 through 20) and one of the 3' primers (SEQ ID NO:17). The 5' primers contain a Sac I restriction site and the 3' primers contain the Xba I restriction site.

Amplification primers designed to amplify human light chain variable regions of the lambda isotype are also contemplated.

All primers and synthetic polynucleotides described herein, were purchased from Oligos etc. (Wilsonville, Oreg.). The pComb 3 expression vector was provided as a gift from Dr. Carlos Barbas III of the Scripps Research Institute, La Jolla, Calif.

$V_H$ and $V_L$ Library Construction

Total RNA was extracted from $1.15 \times 10^7$ lymphocytes using standard guanadinium isothiocynate extraction protocols. See, for example, Chomcynski, P. and Saochi, N., *Anal. Biochem.* 162:156–159 (1987), incorporated herein by reference.

In preparation for PCR amplification, the RNA, prepared above, is used as a template for cDNA synthesis by a primer extension reaction. Thus, 10 $\mu$g RNA was reverse transcribed to single-stranded cDNA using 1 $\mu$g oligo-dT primer with 10 mM dithiothreitol, RNasin™ (a protein RNase inhibitor of Promega Corporation, Madison, Wis.), 25 mM each dATP, dCTP, dGTP, dTTP, 1× reverse transcriptase buffer (Bethesda Research Laboratories, Bethesda, Md.), and 2 $\mu$l (two hundred units) reverse transcriptase (Superscript, Bethesda Research Laboratories) in 50 $\mu$l volume for 10 minutes at room temperature followed by 50 minutes at 42° C. Following a 5 minute 90° C. heat kill and 10 minutes on ice, the reaction was treated with 1 $\mu$l (one unit) RNase H (Bethesda Research Laboratories) for 20 minutes at 37° C.

The single-stranded cDNA generated above was amplified using the polymerase chain reaction ("PCR") method. Family specific variable region and isotype specific constant region primers as described below were used to create heavy chain IgG1 $V_H1–V_H6$ and kappa light chain $V_L1–V_L3$ specific libraries:

Primer to create IgG1 heavy chain constant region library:
CG1Z 5' GCATGTACTAGTTTTGTCACAA-GATTTGGG 3' (SEQ ID NO:9)

Primers to create heavy chain variable region library:
$V_H$1a 5' CAGGTGCAGCTCGAGCAGTCTGGG 3' (SEQ ID NO:10)
$V_H$2f 5' CAGGTGCAGCTACTCGAGTCGGG 3' (SEQ ID NO:11)
$V_H$3a 5' GAGGTGCAGCTCGAGGAGTCTGGG 3' (SEQ ID NO:12)
$V_H$3f 5' GAGGTGCAGCTGCTCGAGTCTGGG 3' (SEQ ID NO:13)
$V_H$4f 5' CAGGTGCAGCTGCTCGAGTCGGG 3' (SEQ ID NO:14)
$V_H$6a 5' CAGGTACAGCTCGAGCAGTCAGG 3' (SEQ ID NO:15)
$V_H$6f 5' CAGGTACAGCTGCTCGAGTCAGGTCCA 3' (SEQ ID NO:16)

Primer to create Kappa light chain constant region library:
$C_K$1d 5' GCGCCGTCTAGAACTAACACTCTCCCCT-GTTGAAGCTCTTTGTGACGGGCGATCTCAG 3' (SEQ ID NO:17)

Primer to create Kappa light chain variable region library:
$V_K$1a 5' GACATCGAGCTCACCCAGTCTCCA 3' (SEQ ID NO:18)
$V_K$2a 5' GATATTGAGCTCACTCAGTCTCCA 3' (SEQ ID NO:19)
$V_K$3a 5' GAAATTGAGCTCACGCAGTCTCCA 3' (SEQ ID NO:20)

PCR amplification is performed in a 100 $\mu$l reaction containing the products of the reverse transcription reaction (about 1 $\mu$l of 450 $\mu$l reaction of the single-stranded cDNA), 60 pm of 3'$V_H$ primer (SEQ ID NO:9), 60 pm of the 5' primer (one of SEQ ID NOS:10 through 16), 8 $\mu$l of the mixture of dNTP's at 25 mM each, 10 $\mu$l of 10×PCR Buffer (Perkin-Elmer), and 5 units of Tag DNA polymerase (Perkin-Elmer, Norwalk, Conn.). The reaction mixture is subjected to 30 cycles of amplification using a Perkin-Elmer 9600 thermocycler. Each amplification cycle included denaturing of cDNA at 94° C. for 15 seconds, followed by annealing of primers at 52° C. for 50 seconds, and amplification at 72° C. for 90 seconds. This was followed by a 10 minute extension at 72° C. Efficient and reproducible DNA homolog synthesis was achieved with the primers defined herein, producing amplified cDNA $V_H$-encoding homologs having a major band of about 680 bp and amplified cDNA $V_K$-coding homologs having a major band at about 660 bp.

After verifying by agarose gel electrophoresis that all amplifications were successful and that similar yields were achieved, the $V_H$-encoding and $V_L$-encoding DNA homologs were separately pooled and gel purified on 0.8% Seaplaque GTG Agarose (FMC, Rockland, Me.) according to the manufacturer's directions.

Ligation of VT-encoding DNA Homologs into Vector

Equal portions of the products from each light chain primer extension reaction were mixed to generate a pooled $V_L$ library of UC$^+$. The pooled $V_L$ library was double-digested with 70 units XbaI per microgram pooled $V_L$ library and 35 units SacI per microgram pooled $V_L$ library. (All restriction enzymes are available from Boehringer-Mannheim, Indianapolis, Ind.) Digested products were again gel purified as described above, and the region of the gel containing DNA fragments of about 660 bp was excised, extracted from agarose and ethanol precipitated. The resulting $V_L$ DNA homologs represent a repertoire of kappa light chain polypeptide genes having cohesive termini adapted for directional ligation to the pComb 3 phagemid Lc2 expression cassette.

The pComb 3 phagemid Lc2 expression cassette is prepared for inserting a light chain DNA homolog by admixing 30 µg of the phagemid to a solution containing 280 units of Xba I and 160 units of Sac I restriction endonucleases and a buffer recommended by the manufacturer. This solution was maintained at 37° C. for 3 hours. The solution was precipitated with 2 ml glycogen, ⅒ volume 3M NaAc, 2.5 volume ethanol, at −20° C. for 1 hour, then pelleted and washed with 70% ethanol. The pellet was re-suspended in water and gel purified on 0.8% 1× TAE Seplaque 676. A 4 Kb band was excised, phenol extracted, LiCl₃ treated and ethanol precipitated the same as PCR products.

The Lc2 expression cassette was then ready for ligation with the $V_L$-encoding DNA homologs prepared above. These $V_L$-encoding DNA homologs were then directly inserted into the Xba I and Sac I restriction digested Lc2 expression cassette by ligating 0.45 µg of $V_L$ DNA homolog into 1.4 µg of digested pComb 3 (kindly provided by Dr. Carlos Barbas III of the Scripps Research Institute, La Jolla, Calif. and described in Barbas et al., *Proc. Natl. Acad. Sci. USA* 88:7978–7982 (1991), incorporated herein by reference) using 10 units ligase in 200 µl volume ligase buffer stored overnight at 25° C., and then heat killed by maintaining at 65° C. for 15 minutes (Boehringer-Mannheim). DNA was precipitated, washed with 70% ethanol, and re-suspended in 15 µl 10 mM MgCl₂.

Transformation of Host with Vector Containing $V_L$-Library

*Escherichia coli* XLI-Blue cells (Stratagene, La Jolla, Calif.) were transformed with re-suspended DNA by electroporation: 300 µl of stock made by concentrating 1 liter of *E. coli* OD$_{600}$=0.8 down to 4 ml of cells were electroporated with 15 µl DNA (≈2 µg) (all of ligation mix). Transformed cells were selected for by plasmid antibiotic resistance by growth super broth containing 100 µg/ml carbenicillin. The library size was 8.6×10$^7$ transformants with 6% background re-ligation.

Antibiotic resistant colonies were amplified by growth in liquid cultures at 37° C. in super broth ("SB") medium (30 g tryptone, 20 g yeast extract, and 10 g 3[N-Morpoholino] propane-sulfonic acid (Mops) per liter of water, adjusted to pH 7) supplemented with 10 µg/ml tetracycline, 20 µg/ml carbenicillin, 40 mM glucose and 10 mM MgCl₂. pComb 3 phagemids encoding a kappa $V_L$ polypeptide ("Kappa-pComb 3 phagemid") were isolated using Qiagen-tips™, an anion-exchange resin of Qiagen, Chatsworth, Calif. following manufacturer instructions. Isolated Kappa-pComb 3 phagemids were double-digested with 10 units XhoI and 3 units SpeI per microgram Kappa-pComb 3 phagemid. Reaction mix was ethanol precipitated and 4.7 Kb double cut phagemid was gel purified on 0.8%. Seaplaque TAE gel as before. The Kappa-pComb 3 phagemids were now ready for ligation with the heavy chain library.

Ligation of $V_H$-encoding DNA Homologs into Vector and Transformation of Host

Equal portions of the products form each heavy chain primer extension were mixed to generate a pooled $V_H$-encoding DNA homolog library. The pooled $V_H$ library was prepared for ligation into the Hc2 expression cassette of the Kappa-pComb 3 phagemid by digestion with Xho I and Spe I nucleases. Accordingly, the pooled $V_H$ library was double-digested with 70 units XhoI and 17 units SpeI per microgram pooled $V_H$ library. Then, 0.40 µg digested heavy chain library was ligated with 1.4 µg digested Kappa-pComb 3 phagemid, described above, using 10 units ligase in 200 µl volume ligase buffer. The reaction was stopped by a heat kill at 65° C. for 15 minutes. DNA was precipitated, the pellet re-suspended in 15 µl 10 mM MgCl₂ and used to electroporate *E. coli* XLI-Blue cells. Electroporated cells were grown in SB, supplemented as described above, except that glucose was not included. The library size was 4.9×10$^7$ with 14% background re-ligation after heavy chain cloning. Presence of both $V_H$- and $V_L$-encoding DNA homologs in the vector was verified by restriction analysis, seven out of seven clones contains both homologs.

Ten milliliter cultures of electroporated *E. coli* XLI-Blue cells were then transferred to SB supplemented with 50 µg/ml carbenicillin, 10 µg/ml tetracycline, and 10 mM MgCl₂ and incubated for another hour. Cultured cells were then infected with 10$^{12}$VCS-M13 helper phage (Stratagene, La Jolla, Calif.) to initiate the generation of copies of the sense strand of the phagemid DNA. After adding helper phage the mixture was added to 100 ml of SB supplemented with 50 µl/ml carbenicillin, 10 µl/ml tetracycline, and 10 mM MgCl₂. The admixture containing the helper phage was then maintained for an additional 2 hours at 37° C. to allow for filamentous bacteriophage assembly wherein the expressed heterodimeric antibody material of UC$^+$ fused to cpIII bacteriophage anchor domain were incorporated into the surface of the bacteriophage particle. After 2 hours the mixture was spiked with 70 µg/ml kanamycin to select for helper phage infected *E. coli* and then allowed to grow overnight at 37° C., 300 rpm. The phage were precipitated by centrifugation resulting in a bacterial cell pellet and a supernatant containing phage, with the titer of colony-forming units ("CFU") determined by plating on LB plates with 100 µg/ml carbenicillin.

EXAMPLE XVI

PANNING

Each well of a 24-well microtiter plate was coated with methanol-fixed neutrophils by adding 10$^6$ neutrophils, allowing them to settle, air dry and then fixing with 100% methanol. Each well was blocked for one hour at 37° C. with 3% bovine serum albumin ("BSA") in Tris-buffered saline ("TBS"). Blocking solution was removed and 5×10$^{11}$ phage in 250 µl TBS was added and allowed to incubate for two hours at 37° C. After washing, acid elution, and neutralization, the number of phage eluted was monitored by CFU.

Eluted phage were amplified by reinfecting *E. coli* XLI-Blue and the panning/amplification cycle repeated five times until there was at least 100 fold enrichment. In this manner a library of phage enriched for p-ANCA material having immunoreactivity with neutrophil antigen was generated. For enrichment quantitation, aliquots of the original library were re-panned in parallel with each cycle of enrichment to control for daily fluctuations in phage recovery. Enrichment was calculated by ratio of phage on vs. off and compared to the unenriched library run on the same day. Panning was also performed in a 96 well format with $10^{11}$ phage per well to compare formats.

EXAMPLE XVII

PREPARATION OF SOLUBLE RECOMBINANT ANTI-NEUTROPHIL ANTIBODY MATERIAL OF UC AND LIBRARY SCREENING

Preparation of soluble heterodimeric antibody material, specifically Fab, was performed by isolating phagemid using Qiagen-tips™ in accordance with the manufacturer's instructions. (Qiagen, Chatsworth, Calif.) Isolated phagemid was then digested with 17 units SpeI and 50 units NheI per microgram of phagemid to remove cpIII gene segment. The phagemid DNA was then gel-purified and self-ligated by using 10 units ligase per 1 µg phagemid and maintaining the reaction mixture overnight at 25° C. The reaction was stopped by maintaining it at 65° C. for 15 minutes. 200 ng gel purified fragment was self ligated in 20 µl volume and used to transform $E.$ $coli$ XLI-Blue by electroporation at 0° C. in 0.2 cm gap curette at 2.5 kV, 25 µF and 200 R using 40 µl of $E.$ $coli$ stock and 1 µl of ligation mix. Single colonies were picked from an LB agar plates containing 100 µl/ml carbenicillin and grown in 10 ml SB supplemented with 10 µg/ml tetracycline, 50 µg/ml carbenicillin, and 20 mM $MgCl_2$ for six hours. Cultures were then induced by the addition of 1 mM isopropyl 6-D-thiogalactopyranoside ("IPTG") (United States Biochemicals, Cleveland, Ohio) and grown overnight. The phage were isolated by centrifugation resulting in a bacterial cell pellet and a supernatant containing phage. The supernatant was removed and analyzed for Fab production by kappa-capture ELISA as described above, detecting with goat anti-human Fab-alkaline phosphatase (Pierce, Rockland, Ill.). Ten clones each from the enriched and unenriched libraries were selected for comparison. Six out of the ten clones from the unenriched library produced significant amounts of Fab as assayed by kappa-capture ELISA. In contrast, ten out of ten clones from the enriched library produced Fab, indicating that the enriched library had positively selected for Fab expression.

These clones were also analyzed for neutrophil binding by alcohol-fixed neutrophil ELISA. None of the ten clones from the unenriched library bound neutrophil, whereas all samples clones from the enriched library demonstrated avid neutrophil binding.

Diversity of heavy and light chain usage in Fabs from enriched and unenriched libraries were monitored by digesting 4 µg of phagemid encoding a single Fab with 20 units of BSTN1 (New England Biolabs, Beverly, Mass.) and analyzing fragments on a 3% agarose gel. Each of thirty clones from the unenriched library showed a distinct restriction pattern, whereas the clones from the enriched library displayed only two clonal patterns. Clones representative of these two patterns (5-3 and 5-4) were therefore directly analyzed by DNA sequencing, as described below.

EXAMPLE XVIII

PURIFICATION OF FAB

Both enriched and unenriched libraries were transferred from pComb 3 to $C_3AP313H_6$, a pComb 3 derivative which fuses six histidine to the carboxy terminus of the Fab after SpeI and NheI digestion to remove the cpIII anchor domain. ($C_3AP313H_6$ was a gift of Carlos Barbas III, Scripps Research Institute, La Jolla, Calif.). Libraries were moved by removing the $V_H$- and $V_L$-encoding polynucleotides from the Hc2 and Lc2 expression cassettes of pComb 3 and sequentially ligating them into $C_3AP313H_6$. $E.$ $coli$ XLI-Blue cells were transformed with the new phagemid by electroporation. Individual colonies were isolated by LB agar selection supplemented with 100 µl/ml carbenicillin.

The 5-3 clone from the enriched library was chosen for large scale purification. A single colony was picked and allowed to grow overnight in 10 ml SB, supplemented with 10 µg/ml tetracycline, 50 µg/ml carbenicillin, 10 mM $MgCl_2$, and 40 mM glucose. The bacterial culture was pelleted by centrifugation to remove glucose and the cell pellet transferred into one liter of SB containing 50 µg/ml carbenicillin and 20 mM $MgCl_2$. The XL1-Blue cells were grown at 37° C. shaking at 300 rpm until absorbance ($OD_{600}$) was between 0.6–0.8. The cell culture was then induced with 4 mM IPTG to express the heterodimeric antibody material and grown at 30° C. overnight. The cell culture was centrifuged to pellet the XL1-Blue cells and the pellet re-suspended in 30 ml sonication buffer (50 mM $NaPO_4$, 300 mM $NaCl_2$, 0.01% $NaN_3$, pH 7.9). The re-suspended cells were sonicated eight times in 15 seconds bursts at 50% power (40 watts micro sonic disrupter, Tekmar, Cincinnati, Ohio).

The sonicate was centrifuged at 15,000 rpm in a Beckman JA-20 centrifuge for 40 min at 4° C. and the supernatant serially filtered through a 0.45 and a 0.22 micron Nytex filter (Amicon, Beverly, Mass.). Sonicate was immediately loaded at 20 ml/hr on a 1 ml NTA-Ni column (Qiagen) and washed with sonication buffer, typically 40–50 ml, until absorbance ($OD_{280}$) was <0.01. The column was then washed with 10 ml of 10 mM imidazole in sonication buffer to remove contaminants, followed with 10 ml each of 100 mM, 250 mM, and 500 mM imidazole collecting 1 ml fractions monitored by $OD_{280}$. Aliquots were analyzed by SDS-PAGE 12% denaturing and reducing gel to determine where Fab eluted. Due to the presence of imidazole, samples with loading dye were not boiled, but denatured instead at 37° C. for 10 min before loading. Typically, the Fab elutes in first 3 fractions of the 100 mM imidazole wash.

One milliliter fractions that contain Fab were then pooled and dialyzed (6–8 kD cutoff membranes) using Amicon dialysis membranes against PBS to remove imidazole. Samples were concentrated and any free heavy or light chain removed using a Centricon 50™, centrifugation-dialysis membrane from Amicon Corporation, Beverly, Mass.

Curiously, the calculated antibody level in the purified fraction differed with total protein (Bio-rad Protein Assay, Richmond, Calif.) versus ELISA (anti-Kappa) determination. Per 1 liter bacterial culture, Fab yield was ~1 mg by total protein assay, versus ~0.1 mg by immunoassay. Since use of the proteins in this study utilized ELISA immunoreactivity, Fab concentrations are reported using the ELISA method.

The 5-3 Fab was characterized using the assays described herein. Strong binding (approx. 0.1 micrograms/milliliter) to fixed neutrophil in an ELISA format. It is also notable that 5-3 p-ANCA Fab is avid compared to UC serum, since optimal binding occurred at 1% serum (or approx. 0.1 milligrams/milliliter total IgG). Estimating that approx. 1% hyperimmune serum is antigen-specific, then the level of native p-ANCA IgG is approx. 1 microgram/ml, or similar in range to binding by monovalent Fab.

In inflammatory disorders, ANCA-type marker antibodies are specific for certain defined neutrophil proteins. The 5-3 p-ANCA Fab was tested for immunoreactivity with cathespin G, elastase, myeloperoxidase and lactoferrin in an ELISA format. No binding was detected up to 500 nanograms/ml of 5-3 p-ANCA Fab.

The 5-3 p-ANCA Fab was also tested by alcohol-fixed neutrophil IIF assay for the p-ANCA staining pattern. Immunofluorescent detection of neutrophil staining by 5-3 p-ANCA Fab yielded the same p-ANCA staining pattern produced by conventional UC serum. When the immunoreactivity of 5-3 p-ANCA Fab was tested for DNAase sensitivity in accordance with EXAMPLE VI above, as with conventional p-ANCA seropositive UC serum, DNAase I treatment of neutrophil caused the complete loss of detectable p-ANCA staining pattern. In addition, confocal microscopy demonstrated that 5-3 p-ANCA Fab binds antigen located inside the nuclear envelop, a characteristic found in p-ANCA seropositive UC serum.

EXAMPLE XIX

NUCLEIC ACID SEQUENCING

Nucleic acid sequencing was carried out on doublestranded DNA of the 5-3 and 5-4 clones using 5' and 3' primers for the heavy and light chains (SEQ ID NOS:21 and 22, and SEQ ID NOS:23 and 24, respectively) and Sequenase 1.0 (United States Biochemicals). Homology searches and lineups were performed using Genebank.

Although the invention has been described with reference to presently preferred embodiments, it should be understood that various modifications can be made without departing from the spirit of the invention.

We claim:

1. A method of measuring the presence or absence of perinuclear anti-neutrophil cytoplasmic antibodies (p-ANCA) associated with ulcerative colitis, primary sclerosing cholangitis, or type 1 autoimmune hepatitis in a sample, said method comprising:

(a) contacting the sample and one or more secondary antibodies, wherein at least one secondary antibody is a detectable secondary antibody, with DNAase-treated fixed neutrophils and control fixed neutrophils, under conditions suitable to form a complex of neutrophil, p-ANCA and said detectable secondary antibody, wherein said DNAase-treated fixed neutrophils are neutrophils which have been subjected to DNAase under conditions sufficient to cause substantially complete digestion of cellular DNA without significant loss of nuclear or cellular morphology prior to said contacting step, wherein said control fixed neutrophils are neutrophils which have not been subjected to DNAase, and wherein at least one of said secondary antibodies has specificity for a class determining portion of p-ANCA;

(b) separating unbound secondary antibody from the complex;

(c) assaying for a pattern of p-ANCA immunoreactivity in said DNAase-treated fixed neutrophils and in said control fixed neutrophils by detecting the presence, absence or a pattern of complexed secondary antibody; and (d) comparing the pattern of p-ANCA immunoreactivity in said DNAase-treated fixed neutrophils to the pattern of p-ANCA immunoreactivity in said control fixed neutrophils, wherein absence of a perinuclear staining pattern in said DNAase-treated fixed neutrophils and presence of a perinuclear staining pattern in said control fixed neutrophils indicates the presence of p-ANCA associated with ulcerative colitis in said sample, wherein presence of a homogenous cytoplasmic staining pattern in said DNAase-treated fixed neutrophils and a pernuclear staining pattern in said control fixed neutrophils indicates the presence of p-ANCA associated with primary sclerosing cholangitis in said sample, and wherein presence of a granular cytoplasmic staining pattern in said DNAase-treated fixed neutrophils and a perinuclear staining pattern in said control fixed neutrophils indicates the presence of p-ANCA associated with type 1 autoimmune hepatitis.

2. The method of claim 1, wherein said DNAase-treated fixed neutrophils and said control fixed neutrophils are alcohol-fixed neutrophils.

3. The method of claim 2, wherein said alcohol-fixed neutrophils are methanol-fixed neutrophils.

4. A method according to claim 3, wherein the conditions sufficient to cause substantially complete digestion of cellular DNA, without substantial loss of nuclear or cellular morphology, comprise incubating said neutrophils in a concentration of DNAase of about 2 to 10 units of DNAase per milliliter of buffer for a time in the range of about 15 minutes to one hour at a temperature in the range of about 22° C. to 40° C.

5. A method according to claim 3, wherein the conditions sufficient to cause substantially complete digestion of cellular DNA, without substantial loss of nuclear or cellular morphology, comprise incubating said neutrophils in a concentration of DNAase of about 3 units of DNAase per milliliter buffer for 30 minutes at 37° C.

6. A method according to claim 1, wherein at least one of said secondary antibodies is anti-IgG.

7. A method according to claim 6, wherein the DNAase-treated fixed neutrophils and control fixed neutrophils are human neutrophils and the sample is human blood serum.

8. A method according to claim 7, wherein the anti-IgG is anti-human IgG.

9. A method according to claim 1, wherein the detectable secondary antibody is detectable by detecting enzymatic conversion, radioactivity, fluorescence or color.

10. A method according to claim 9, wherein the secondary antibody is linked to an enzyme.

11. A method according to claim 10, wherein the enzyme is alkaline phosphatase.

12. A method according to claim 9, wherein the secondary antibody is linked to a fluorogenic substance.

13. A method according to claim 12, wherein the fluorogenic substance is fluorescein isothiocyanate.

14. A method of differentiating the conditions of ulcerative colitis without primary sclerosing cholangitis, primary sclerosing cholangitis with or without concomitant UC, Crohn's disease and type 1 autoimmune hepatitis, said method comprising:

(a) contacting DNAase-treated fixed neutrophils and control fixed neutrophils with a sample and a detectable secondary antibody under conditions suitable to form an immune complex of neutrophil, p-ANCA and detectable secondary antibody, wherein cellular DNA of the DNAase-treated fixed neutrophils has been digested by DNAase without significant lose of nuclear or cellular morphology, wherein said control fixed neutrophils are neutrophils which have not been subjected to DNAase, and wherein the detectable secondary antibody is specific for a class determining portion of p-ANCA;

(b) separating unbound secondary antibody from the immune complex;

(c) detecting a staining pattern in said DNAase-treated fixed neutrophils and in said control fixed neutrophils; and (d) comparing the staining pattern in said DNAase-treated fixed neutrophil to the staining pattern in said control fixed neutrophils;

wherein loss of detectable complex associated with perinuclear staining pattern in said DNAase-treated fixed neutrophils, as compared to said control fixed neutrophils, indicates ulcerative colitis without primary sclerosing cholangitis, wherein conversion of detectable complex associated with perinuclear staining pattern to homogenous cytoplasmic staining pattern, in said DNAase-treated fixed neutrophils, as compared to said control fixed neutrophils, indicates primary sclerosing cholangitis without ulcerative colitis or primary sclerosing cholangitis with concomitant ulcerative colitis, wherein conversion of detectable complex associated with perinuclear staining pattern to granular cytoplasmic staining pattern, in said DNAase-treated fixed neutrophils, as compared to said control fixed neutrophils, indicates type 1 autoimmune hepatitis, and wherein absence of a detectable complex associated with perinuclear staining pattern in said control fixed neutrophils indicates Crohn's disease.

15. A method of detecting the presence of perinuclear anti-neutrophil cytoplasmic antibody (p-ANCA) associated with type 1 autoimmune hepatitis in a sample, said method comprising:

(a) contacting DNAase-treated fixed neutrophils and control fixed neutrophils with said sample and a detectable secondary antibody under conditions suitable to form an immune complex of neutrophil, p-ANCA and detectable secondary antibody, wherein said DNAase-treated fixed neutrophils are neutrophils which have been subjected to DNAase under conditions sufficient to cause substantially complete digestion of cellular DNA without significant loss of nuclear or cellular morphology, wherein said control fixed neutrophils are neutrophils which have not been subjected to DNAase, and wherein the detectable secondary antibody is specific for a class determining portion of p-ANCA;

(b) separating unbound secondary antibody from the immune complex;

(c) detecting a staining pattern in said DNAase-treated fixed neutrophils and in said control fixed neutrophils; and (d) comparing the staining pattern in said DNAase-treated fixed neutrophils to the staining pattern in said control fixed neutrophils, wherein presence of a granular cytoplasmic staining pattern in the DNAase-treated fixed neutrophils and a perinuclear staining pattern in the control fixed neutrophils, indicates the presence of p-ANCA associated with type 1 autoimmune hepatitis in the sample.

16. The method of claim 15, wherein said DNAase-treated fixed neutrophils and control fixed neutrophils are alcohol-fixed neutrophils.

17. The method of claim 16, wherein said alcohol-fixed neutrophils are methanol-fixed neutrophils.

18. A method according to claim 17, wherein the conditions sufficient to cause substantially complete digestion of cellular DNA, without substantial loss of nuclear or cellular morphology, comprise incubating said neutrophils in a concentration of DNAase of about 2 to 10 units of DNAase per milliliter of buffer for a time in the range of about 15 minutes to one hour at a temperature in the range of about 22° C. to 40° C.

19. A method according to claim 18, wherein the detectable secondary antibody is detectable anti-IgG.

20. A method of differentiating primary sclerosing cholangitis from type 1 autoimmune hepatitis, said method comprising:

(a) contacting DNAase-treated fixed neutrophils and control fixed neutrophils with a sample and a detectable secondary antibody under conditions suitable to form an immune complex of neutrophil, p-ANCA and detectable secondary antibody, wherein said DNAase-treated fixed neutrophils are neutrophils which have been subjected to DNAase under conditions sufficient to cause substantially complete digestion of cellular DNA without significant loss of nuclear or cellular morphology, wherein said control fixed neutrophils are neutrophils which have not been subjected to DNAase, and wherein the detectable secondary antibody is specific for a class determining portion of p-ANCA:

(b) separating unbound secondary antibody from the immune complex;

(c) detecting a staining pattern in said DNAase-treated fixed neutrophils and in said control fixed neutrophils; and (d) comparing the staining pattern in said DNAase-treated fixed neutrophils to the staining pattern in said control fixed neutrophils, wherein presence of a homogeneous cytoplasmic staining pattern in the DNAase-treated fixed neutrophils and a perinuclear staining pattern in the control-fixed neutrophils indicates primary sclerosing cholangitis, and wherein presence of a granular cytoplasmic staining pattern in the DNAase-treated fixed neutrophils and a perinuclear staining pattern in the control fixed neutrophils indicates type 1 autoimmune hepatitis.

21. The method of claim 20, wherein said DNAase-treated fixed neutrophils and control fixed neutrophils are alcohol-fixed neutrophils.

22. The method of claim 21, wherein said alcohol-fixed neutrophils are methanol-fixed neutrophils.

23. A method according to claim 22, wherein the conditions sufficient to cause substantially complete digestion of cellular DNA, without substantial loss of nuclear or cellular morphology, comprise incubating said neutrophils in a concentration of DNAase of about 2 to 10 units of DNAase per milliliter of buffer for a time in the range of about 15 minutes to one hour at a temperature in the range of about 22° C. to 40° C.

24. A method according to claim 23, wherein the detectable secondary antibody is detectable anti-IgG.

* * * * *

UNITED STATES PATENT AND TRADEMARK OFFICE
CERTIFICATE OF CORRECTION

PATENT NO. : 5,830,675
DATED : November 3, 1998
INVENTOR(S) : Targan et al.

Page 1 of 2

It is certified that error appears in the above-identified patent and that said Letters Patent is hereby corrected as shown below:

Column 1,
Line 66, please delete "CD not" and replace with -- CD are not --.

Column 3,
Line 60, please delete "neutrophil-" and replace with -- neutrophil. --.

Column 4,
Line 12, please delete "antibodies".

Column 5,
Line 43, please delete "bining" and replace with -- binding --.

Column 8,
Line 6, please delete "combinatorialy" and replace with -- combinatorial --.

Column 11,
Line 59, please delete "Type I" and replace with -- Type 1 --.

Column 12,
Line 51, please delete "Type I" and replace with -- Type 1 --.

Column 13,
Line 33, please delete "Type I" and replace with -- Type 1 --.
Line 53, please delete "Type I" and replace with -- Type 1 --.
Line 57, please delete "Type I" and replace with -- Type 1 --.

Column 14,
Line 11, please delete "Type I" and replace with -- Type 1 --.
Line 40, please delete "Type I" and replace with -- Type 1 --.

Column 12,
Line 65, please delete "Neutrophils", replace with -- neutrophils --

Column 16,
Line 6, please delete "-200°" and replace with -- -20° --.

Column 19,
Line 48, please delete "0.056 Tween." and replace therefor with -- 0.05% Tween --.

Column 22,
Line 30, please delete "for further" and replace with -- further for --.

UNITED STATES PATENT AND TRADEMARK OFFICE
CERTIFICATE OF CORRECTION

PATENT NO. : 5,830,675
DATED : November 3, 1998
INVENTOR(S) : Targan et al.

It is certified that error appears in the above-identified patent and that said Letters Patent is hereby corrected as shown below:

Column 26,
Line 4, please delete "0.8%." and replace with -- 0.8% --.
Line 9, please delete "form" and replace with -- from --.

Signed and Sealed this

Twenty-seventh Day of November, 2001

Attest:

*Attesting Officer*

NICHOLAS P. GODICI
*Acting Director of the United States Patent and Trademark Office*